United States Patent [19]

D'Alelio, deceased

[11] Patent Number: 4,517,354
[45] Date of Patent: May 14, 1985

[54] POLYSULFONE COMPOSITIONS AND DERIVATIVES THEREOF

[75] Inventor: Gaetano F. D'Alelio, deceased, late of South Bend, Ind., by St. Joseph Bank and Trust Company, executor

[73] Assignee: Plastics Engineering Company, Sheboygan, Wis.

[21] Appl. No.: 547,021

[22] Filed: Oct. 31, 1983

Related U.S. Application Data

[63] Continuation-in-part of Ser. No. 280,950, Jul. 6, 1981, abandoned.

[51] Int. Cl.³ .................. C08G 69/32; C08G 69/40; C08G 69/42
[52] U.S. Cl. .................. 528/172; 528/171; 528/173; 549/241; 560/11; 560/12; 560/13; 562/429; 562/430; 564/154; 568/31; 568/33; 568/34
[58] Field of Search .................. 528/171, 172, 173; 549/241; 560/11, 12, 13; 562/429, 430; 564/154; 568/31, 33, 34

[56] References Cited

U.S. PATENT DOCUMENTS 3,753,948  8/1973  Brode et al. .................. 528/173

Primary Examiner—Lester L. Lee
Attorney, Agent, or Firm—Walter J. Monacelli

[57] ABSTRACT

The compositions disclosed herein comprise compounds of the formula:

$$DOOCArO\text{-}ArSO_2Ar'QAr'SO_2Ar\text{-}OArCOOD \quad (I)$$

and also derivatives and polymers therefrom or from the compound:

$$X\text{-}ArSO_2Ar'QAr'SO_2Ar\text{-}X$$

in which compounds D is hydrogen, halogen or a monovalent hydrocarbon radical, preferably of 1–20 carbon atoms; Q is either —O— or —SO$_2$—; Ar and Ar' are divalent aromatic groups including a multiplicity of aromatic groups linked by O, SO$_2$, hydrocarbon groups, etc.; and X is preferably Cl but may be other halogen atoms. In these compounds, the central core or residue —ArSO$_2$Ar'QAr'SO$_2$Ar— may be represented by A. Various derivatives and polymers having the core A are prepared, such as diamides of the formula R$_2$NOCArO-A-OArCONR$_2$; polyester polymers of the formula [—OROOCArO-A-OArCO—]; polyarylate polymers of the formula [—ArCOOArO-A-OArOOCArCOO—]; polycarbonate polymers of the formula [—OCOOArO-A-OArOOCO—]; phenolic resins, and many other derivatives. These compositions exhibit many desirable properties and have many uses including the improvement or upgrading of polyethylene terephthalate (PET) and polybutyleneterephthalate (PBT) resins when blended therewith.

30 Claims, No Drawings

POLYSULFONE COMPOSITIONS AND DERIVATIVES THEREOF

This application is a continuation-in-part of application Ser. No. 280,950 filed July 6, 1981, and now abandoned.

BACKGROUND OF THE INVENTION

1. Field of the Invention

This invention relates to various polysulfone derivatives. More specifically it relates to monomeric and polymeric derivatives. Still more specifically it relates to such compositions which may be derived from compounds having the formula X—ArSO$_2$Ar'QAr'SO$_2$AR—X wherein the various symbols are as defined herein.

2. State of the Prior Art

Sulfone monomers and polysulfone polymers having the structure —Ar—SO$_2$— therein are known. However applicant is not aware of any prior art showing the specific polysulfone structures described herein.

SUMMARY OF THE INVENTION

In accordance with the present invention, polysulfone compounds have been found which are useful for preparing a variety of derivatives suitable for numerous purposes. These polysulfones have the formula:

DOOCArO—ArSO$_2$Ar'QAR'SO$_2$Ar—OArCOOD    (I)

wherein D represents hydrogen, halogen or a monovalent hydrocarbon group, preferably of 1-20 carbon atoms; Ar and Ar' are divalent aromatic radicals including a multiplicity of aromatic groups linked by O, SO$_2$, divalent hydrocarbon groups, etc., and Q represents O or SO$_2$. These compounds may be prepared by the reaction of a hydroxy aromatic carboxylic ester with X—ArSO$_2$Ar'QAr'SO$_2$Ar—X wherein X is preferably chlorine but may be other halogen atoms, and the other symbols are as defined above. Where D is to represent hydrogen, the ester groups are hydrolyzed to the acid groups. The acid may be converted to the acid halide by reaction with thionyl halide, preferably SOCl$_2$. In these and various other compounds described below, the central core or residue —ArSO$_2$Ar'QAr'SO$_2$Ar— may be represented by A.

In addition to saturated aliphatic, cycloaliphatic and alkylaryl esters the esters of compound I may also include unsaturated esters, such as allyl esters, propargyl esters, vinylaryl esters, propargyl aryl esters, etc.

In the above Formula I where D is defined as hydrogen, halogen or a hydrocarbon group, the halogen may be Br, I, F but is preferably Cl, and the hydrocarbon may be aliphatic, aromatic, cycloaliphatic and combinations of such radicals, including those which have ethylenic or acetylenic unstaturation therein.

The hydrocarbon groups may have attached thereto any group that will not interfere with the preparation and functions of the compounds of this invention as described herein. Preferably these groups are hydrocarbon or a multiplicity of hydrocarbon groups joined by ether, sulfide, ester and sulfonyl groups such as —O—, —S—, —COO—, —OOC—, —S(O)$_2$—, etc.

Typical monovalent hydrocarbon groups suitable in the above formulas include: —CH$_3$, —C$_2$H$_5$, —C$_3$H$_7$, —C$_4$H$_9$, —C$_6$H$_{13}$, —C$_{10}$H$_{21}$, —C$_{18}$H$_{37}$, —C$_6$H$_{11}$, —C$_5$H$_9$, —C$_5$H$_8$CH$_3$, —C$_6$H$_{10}$C$_2$H$_5$, —CH$_2$C$_6$H$_{11}$, —CH$_2$CH$_2$C$_6$H$_{11}$, —C$_6$H$_5$, —C$_6$H$_4$CH$_3$, —C$_6$H$_4$C$_3$H$_7$, —C$_6$H$_3$(CH$_3$)$_2$, —C$_6$H$_5$OCH$_3$, —C$_6$H$_4$OC$_2$H$_5$, —C$_6$H$_4$SCH$_3$, —C$_6$H$_4$OOCCH$_3$, —C$_6$H$_4$SO$_2$C$_6$H$_5$, —C$_6$H$_4$SO$_2$C$_6$H$_4$CH$_3$, —C$_6$H$_4$SO$_2$C$_6$H$_5$, —C$_6$H$_3$(CH$_3$)OC$_3$H$_7$, —C$_6$H$_4$OC$_6$H$_4$CH$_3$, —C$_{10}$H$_8$, —C$_{10}$H$_7$CH$_3$, —C$_{10}$H$_7$C$_2$H$_5$, —C$_{10}$H$_6$(CH$_3$)$_2$, —C$_{10}$H$_6$OCH$_3$, —C$_{10}$H$_6$OOCCH$_3$, —(C$_6$H$_4$)$_3$C$_3$H$_7$, —(C$_6$H$_4$)$_3$OC$_4$H$_9$, —(C$_6$H$_4$)$_3$OC$_6$H$_5$, —C$_6$H$_4$(OCH$_2$CH$_2$)$_2$H, —C$_6$H$_4$(OCH$_2$CH$_2$)$_3$H, —(C$_6$H$_4$O)$_3$C$_3$H$_7$, —CH$_2$CH$_2$OCH$_2$CH$_2$)$_2$H, —CH$_2$CH$_2$(OCH$_2$CH$_2$)$_3$OOCCH$_3$, —CH$_2$CH$_2$OC$_6$H$_5$, —CH$_2$CH$_2$OOCCH$_3$, —CH$_2$CH(CH$_3$)OOCC$_6$H$_5$, —C$_6$H$_4$COOC$_2$H$_5$, —CH$_2$COOC$_6$H$_5$, —C$_6$H$_4$CH=CH$_2$, —C$_6$H$_3$(CH$_3$)CH=CH$_2$, —C$_6$H$_4$C(CH$_3$)=CH$_2$, —C$_6$H$_4$C≡CH, etc.

The divalent aromatic radicals Ar and Ar' are preferably hydrocarbon but can contain additional groups which will not interfere with the various reactions involved in the preparation and use of the products of this invention.

These are divalent benzenoid radicals advantageously selected from the group consisting of:

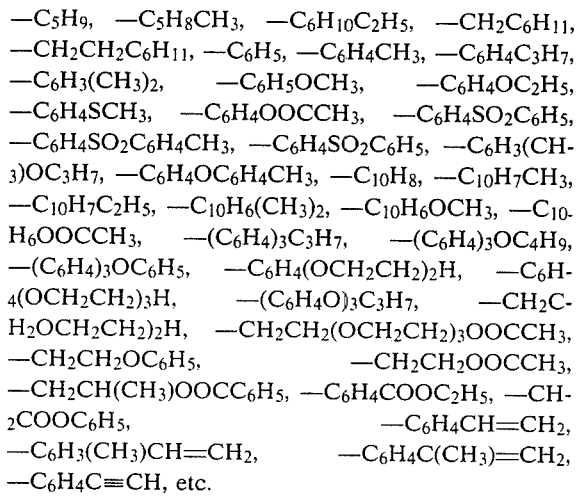

and multiples thereof connected to each other by Z, for example,

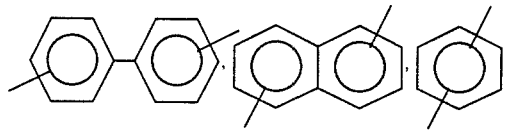

wherein Z is an alkylene chain of 1-3 carbon atoms, —CH=CH—, or; —O—, —S—, —SO$_2$—,

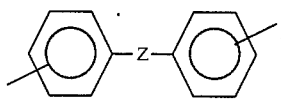

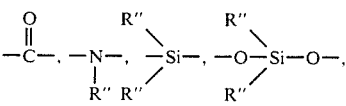

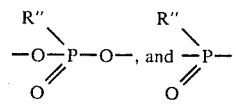

wherein R" is selected from the group consisting of alkyl and aryl groups of 1-20, preferably 1 to 7 carbon atoms. Ar is preferably:

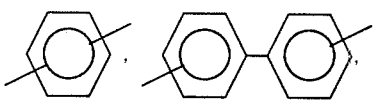

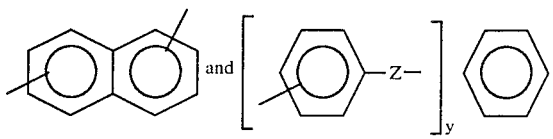 and where Z is an alkylene chain of 1–3 carbon atoms,

—O—, —S—, —CH=CH—, —SO$_2$—, and y is 1 to 3. Particularly preferred for Ar and Ar' is the

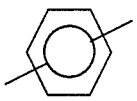

radical.

Typical compounds of the formula X—ArSO$_2$Ar'-QAr'SO$_2$Ar—X which can be used in the preparation of the compositions of this invention include the following:

Cl—C$_6$H$_4$SO$_2$C$_6$H$_4$OC$_6$H$_4$SO$_2$C$_6$H$_4$—Cl
Cl—C$_6$H$_4$SO$_2$C$_6$H$_4$SO$_2$C$_6$H$_4$SO$_2$C$_6$H$_4$—Cl
Cl—C$_6$H$_3$(CH$_3$)SO$_2$C$_6$H$_4$OC$_6$H$_4$SO$_2$C$_6$H$_3$(CH$_3$)—Cl
Br—C$_{10}$H$_6$SO$_2$C$_6$H$_4$OC$_6$H$_4$SO$_2$C$_{10}$H$_6$—Br
Cl—C$_6$H$_4$SO$_2$C$_6$H$_3$(C$_2$H$_5$)SO$_2$C$_6$H$_3$(C$_2$H$_5$)SO$_2$C$_6$H$_4$—Cl
I—C$_6$H$_4$SO$_2$C$_6$H$_4$SO$_2$C$_6$H$_4$SO$_2$C$_6$H$_4$—I
F—C$_6$H$_4$SO$_2$C$_6$H$_4$OC$_6$H$_4$SO$_2$C$_6$H$_4$—F
Cl—C$_6$H$_4$C$_6$H$_4$SO$_2$C$_6$H$_4$OC$_6$H$_4$SO$_2$C$_6$H$_4$C$_6$H$_4$—Cl
Cl—C$_6$H$_4$OC$_6$H$_4$SO$_2$C$_6$H$_4$OC$_6$H$_4$SO$_2$C$_6$H$_4$OC$_6$H$_4$—Cl
Cl—C$_6$H$_4$SO$_2$C$_6$H$_4$SO$_2$C$_6$H$_4$OC$_6$H$_4$SO$_2$C$_6$H$_4$SO$_2$C$_6$H$_4$—Cl
Cl—C$_6$H$_4$CH$_2$C$_6$H$_4$SO$_2$C$_6$H$_4$OC$_6$H$_4$SO$_2$C$_6$H$_4$CH$_2$C$_6$H$_4$—Cl
Cl—C$_6$H$_4$CH=CHC$_6$H$_4$SO$_2$C$_6$H$_4$OC$_6$H$_4$SO$_2$C$_6$CH=CHC$_6$H$_4$—Cl
Br—C$_6$H$_4$SO$_2$C$_{10}$H$_6$SO$_2$C$_{10}$H$_6$SO$_2$C$_6$H$_4$—Br

These may be prepared in accordance with the procedures described below in Examples A and B.

The compounds of Formula I are easily prepared by the reaction of X—ArSO$_2$Ar'QAr'SO$_2$Ar—X (1 mole) with 2 moles of CH$_3$OOCC$_6$H$_4$OH (available commercially as Parasept) preferably in the presence of an anhydrous medium such as dimethyl sulfoxide or other aprotic solvent, and an alkali metal hydroxide, such as NaOH. Other esters may be used in which the methyl group is replaced by other hydrocarbon groups or in which the phenylene (—C$_6$H$_4$—) radical is replaced by other divalent aromatic radicals. Because of economics and availability, Parasept is preferred. The methyl or other hydrocarbon group may be replaced to give the corresponding acid, acid halide or other ester groups by standard methods of hydrolysis, reaction with SOCl$_2$ or ester interchange, respectively.

Various types of polymers may be prepared from the compounds of Formula I. For example, polyesters and polyamides may be prepared by reaction with polyols and polyamines, and additional polymers may be prepared by standard, well known free radical polymerization techniques when the D of the formula contains an unsaturated group, such as vinyl, propargyl, etc.

In conducting polymerizations various solvents may be used with the polysulfones of this invention. The particular solvent used will depend on the specific polysulfone used. In many cases, the solvent may be an aprotic organic compound having a dielectric constant between 35 and 45, preferably one which is water soluble. Representative aprotic compounds are N,N-dimethylformamide, N,N-diethylformamide, N,N-dimethylmethoxyacetamide, N-methyl caprolactam, caprolactam, N,N-dimethylacetamide, N,N-diethylacetamide, dimethyl sulfoxide, N-mexthyl-α-pyrrolidone, tetramethylurea, hexamethylphosphoramide, tetramethylene sulfone, N,N,N',N'-tetramethyl-α-ethylmalonamide, N,N,N',N'-tetramethylglutaramide, N,N,N',N'-tetramethylsuccinamide, thiobis(N,N-dimethylacetamide), bis(N,N-dimethylcarbamylmethyl)ether, N,N,N',N'-tetramethylfuraramide, methylsuccinonitrile, N,N-dimethylcyanoacetamide, N,N-dimethyl-β-cyano-propionamide, N-formylpiperidine and butyrolactone, etc.

Of these solvents, dimethylacetamide is most preferred. Other preferred solvents are dimethylformamide, N-methyl pyrrolidone, dimethyl sulfoxide, butyrolactone and caprolactam.

In many cases, non-aprotic solvents can be used. For example, xylene, phenol, anisole, benzonitrile, acetophenone, methylphenylether or mixtures of these with each other, the aprotic solvents or with relatively poor solvents such as benzene, toluene cyclohexane, cyclohexene, dioxane, butyl cellosolve and the like.

The concentration of the polysulfone in the solvent can be in the range of 1 to 80% by weight of polysulfone and solvent depending on the polysulfone, the solvent and the temperature used. Preferably, the concentration is between 10 and 60% by weight.

Polymerization products of the present invention have application in a wide variety of physical shapes and forms, including use as films, molding compounds, coatings, etc. The unusual heat stability and resistance to deformation at elevated temperatures in the cured state makes these compositions especially unique. When used as films or when made into molded products, these polymers, including laminated products prepared therefrom, not only possess excellent physical properties at room temperature, but they retain their strength and excellent response to work-loading at elevated temperatures for long periods of time.

Moreover, solutions of the curable compositions herein described can be coated on electrical conductors such as copper, aluminum, etc. and thereafter, the coated conductor can be heated at elevated temperatures to remove the solvent and to effect curing of the resinous composition. If desired, an additional overcoat may be applied to such insulated conductors including the use of polymeric coatings such as polyamides, polyesters, silicones, polyvinylformal resins, epoxy resins, polyimides, polytetrafluoro-ethylene, etc.

They can also be used as binders for asbestos fibers, carbon fibers and other fibrous materials in making brake linings. In addition, molding compositions and molded articles may be formed from the polymeric compositions in this invention by incorporating such fillers as asbestos, glass fibers, talc, quartz, powder, wood flour, finely divided carbon, silica, into such compositions prior to molding. Shaped articles are formed under heat, or under heat and pressure in accordance with practices well known in the art. In addition, various heat-resistant pigments and dyes may be incorporated as well as various types of inhibitors, depending on the application intended.

Various other compounds or derivatives of this invention may be prepared from compound I or from the starting dihalide compound X—A—X. For example, compound I may be reacted with an amine, NHR$_2$, to give the compound:

$$R_2NOCArO\text{—}A\text{—}OArCONR_2 \tag{II}$$

wherein R represents hydrogen or a hydrocarbon radical, preferably of 1-20 carbon atoms. When a diamine is used, a polymer is produced having a plurality of repeating units of the structure:

$$-NR\text{—}R'\text{—}NR(O)CArO\text{—}A\text{—}OArC(O)- \tag{III}$$

wherein R' is a divalent aliphatic, cycloaliphatic or aromatic hydrocarbon radical.

Polymeric polyesters may be prepared by reacting compound I with approximately equimolar proportions of a polyol, HOR'OH, such as ethylene glycol, etc. Here again, the R' may be aliphatic, cycloaliphatic or aromatic. The resultant polymers have a repeating unit structure of the formula:

$$-OR'O(O)CArO\text{—}A\text{—}OArC(O)- \tag{IV}$$

Various unsaturated aromatic ether compounds may be prepared by the reaction of vinylaryl, allylaryl and acetylenicaryl hydroxy compounds with X—A—X to give diethers having the formula KO—A—OK (V), wherein K represents an aromatic group having a terminal vinyl or acetylene radical, such as
CH$_2$=CH—Ar—O—A—O—Ar—CH=CH$_2$
CH$_2$=CHCH$_2$ArO—A—OArCH$_2$CH=CH$_2$
CH≡CCH$_2$ArO—A—OArCH$_2$C≡CH
CH$_2$=C(CH$_3$)ArO—A—O—Ar—C(CH$_3$)=CH$_2$ Dihydroxy aromatic compounds may be reacted with approximately equimolar proportions of X—A—X, preferably with at least two moles of dihydroxy compound per mole of X—A—X to give derivatives of the formula:

$$HOArO\text{—}A\text{—}OArOH \tag{VI}$$

These derivatives (VI) may be condensed with aldehydes such as formaldehyde to produce resins having the repeating unit formula:

$$\begin{array}{cc} HO & HO \\ | & | \\ -CH_2ArO\text{—}A\text{—}OArCH_2- \end{array} \tag{VII}$$

Derivatives VI may also be reacted with aromatic dicarboxyl dihalides such as terephthalic dichloride, to give polymers having the repeating unit:

$$-ArO\text{—}A\text{—}OArOOCArCOO- \tag{VIII}$$

or with phosgene, etc., to give polycarbonate polymers having the repeating unit:

$$-ArO\text{—}A\text{—}OArOOCO-. \tag{IX}$$

Reaction of polyesters IV derived from aromatic polyols, such as hydroquinone, p,p'-dihydroxydiphenyl, bis-phenol-A, etc., may be enhanced in heat resistance by reaction with the dihydroxy compounds VI or by the direct preparation of polyesters of very good heat resistance by the reaction of derivative I with the dihydroxy compound VI to give polymers having the repeating unit:

$$-OOCArO\text{—}A\text{—}OArCOOArO\text{—}A\text{—}OAr-. \tag{X}$$

The reaction of X—A—X with HOArNH$_2$, such as HOC$_6$H$_4$NH$_2$ gives the diamine of the formula:

$$NH_2ArO\text{—}A\text{—}OArNH_2 \tag{XI}$$

which, when reacted with the dicarboxy compound I gives a polyamide polymer having repeating units of the formula:

$$-NHARO\text{—}A\text{—}OArNHOCArO\text{—}A\text{—}OArCO_{13} \tag{XII}$$

While the formulas of the preceding compounds of this invention have been given in full, it is possible in view of the generally symmetrical nature of these compounds to abbreviate these by the use of brackets to include the duplicated portions. For example, Formula I can also be written as:

$$[DOOCArO\text{—}ArSO_2Ar']_2Q \tag{I}$$

By reacting the X—A—X compounds with an acyl aromatic hydroxy compound such as a p-acyl-aryl hydroxide, for example m- or p-hydroxy-acetophenone, m- or p-benzoyl-phenol, 3-, 4- or 6-acetyl-naphthol-1,1-, 5- or 6-acetyl-naphthol-2, 4-acetyl-4'-hydroxy-diphenyl, 3-acetyl-4'-hydroxy-diphenyl oxide, etc. Compounds of this invention are preferred having terminal acyl groups. For example, the reaction of p-hydroxy-acetophenone with the X—A—X compound produced below in Example A gives the product:

$$[CH_3COC_6H_4OC_6H_4SO_2C_6H_4]_2O \tag{XIIIa}$$

and with p-hydroxybenzophenone, the product is:

$$[C_6H_5COC_6H_4OC_6H_4SO_2C_6H_4]_2O \tag{XIIIb}$$

With the X—A—X compound produced below in Example B, the products are respectively:

$$[CH_3COC_6H_4OC_6H_4SO_2C_6H_4]_2SO_2 \tag{XIIIc}$$

and $$[C_6H_5COC_6H_4OC_6H_4SO_2C_6H_4]_2SO_2 \tag{XIIId}$$

Also included within the scope of this invention are compounds in which the terminal aromatic groups have a second —COOD group such as Ar(COOR)$_2$, Ar(COOH)$_2$ and Ar(COOX)$_2$. For example, in the preparation described in Example I, the p-hydroxy phenyl benzoate may be replaced by an equivalent amount of 4-hydroxy dimethyl phthalate to give the product $$(CH_3OOC)_2C_6H_3OC_6H_4SO_2C_6H_4OC_6H_4SO_2C_6H_4OC_6H_3(COOCH_3)_2$$

These may be converted to the tetraacids and the tetraacid halides by the procedures described above.

This group of compounds may be represented by the formula:

$$(DOOC)_2ArO\text{—}A\text{—}OAr(COOD)_2 \tag{XIV}$$

In turn these tetrafunctional compounds, by using the techniques described above, may be converted to:

tetraamides: $(R_2NOC)_2ArO-A-OAr(CONR_2)$     (XIVe)

polyamides: 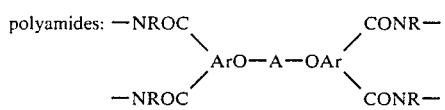     (XIVf)

and unsaturated polymerizable derivatives:

$(CH_2=CHOOC)_2ArO-A-OAr(COOCH=CH_2)_2$     (XIVg)

and $(CH\equiv CCH_2OOC)_2ArO-A-OAr(COOC\equiv CH)_2$     (XIVh)

The polymers of formula XIVf and those produced by free radical polymerization of XIVg and XIVh are tractable products and may be of both thermoplastic and thermosetting types useful as coating materials to give solvent and heat resistant films.

The dicarboxylate groups of formula XIV wherein the members of respective pairs of carboxy groups are positioned ortho or peri to each other may be converted to polyimide polymers by using one mole of a diamine $R'(NH_2)_2$ per mole of formula XIV, which has been first converted to the tetraacid chloride compound by reaction with thionyl chloride. Completion of reaction and removal of by-products and solvent gives a polymer having the repeating unit structure:

     (XV)

The R' in the diamine is preferably aromatic in which case R' may be defined as Ar. Typical diamines of the $NH_2-Ar-NH_2$ formula are those having the Ar groups as defined above.

Examples of aromatic diamines which are suitable to provide the divalent Ar radicals include 4,4'-diaminodiphenyl propane, 4,4'-diamino-diphenyl methane, benzidine, 3,3'-dichlorobenzidene, 4,4'-diaminodiphenyl sulfide, 3,3'-diamino-diphenyl sulfone, 4,4'-diamino-diphenyl sulfone, 4,4'-diamino-diphenyl ether, 1,5-diamino naphthalene, 4,4'-diaminodiphenyl diethylsilane, 4,4'-diamino-diphenyl diphenylsilane, 4,4'-diamino-diphenyl ethyl phosphine oxide, 4,4'-diaminodiphenyl phenyl phosphine oxide, 4,4'-diamino-diphenyl N-methyl amine, 4,4'-diamino-diphenyl N-phenyl amine and mixtures thereof, 3,3'-dimethyl-4,4'-diaminodiphenylmethane, 3,3'-diethyl-4,4'-diaminodiphenylmethane, 3,3'-dimethoxy-4,4'-diaminodiphenylmethane, 3,3'-diethoxy-4,4'-diaminodiphenylmethane, 3,3'-dichloro-4,4',4,4'-diaminodiphenylmethane, 3,3'-dibromo-4,4'-diaminodiphenylmethane, 3,3'-dicarboxy-4,4'-diaminophenylmethane, 3,3'-dihydroxy-4,4'-diaminophenylmethane, 3,3'-disulpho-4,4'-diaminodiphenylmethane, 3,3'-dimethyl-4,4'-diaminodiphenylether, 3,3'-diethyl-4,4'-diaminodiphenylether, 3,3'-dimethoxy-4,4'-diaminodiphenylether, 3,3'-dibromo-4,4'-diamino diphenylether, 3,3'-dicarboxy-4,4'-diaminodiphenylether, 3,3'-dihydroxy-4,4'-diaminodiphenylether, 3,3'-disulfo-4,4'-diaminodiphenylether, 3,3'-dimethyl-4,4'-diaminodiphenylsulfide, 3,3'-diethyl-4,4'-diaminodiphenylsulfide, 3,3'-dimethoxy-4,4'-diaminodiphenylsulfide, 3,3'-diethoxy-4,4'-diaminodiphenylsulfide, 3,3'-dichloro-4,4'-diaminodiphenylsulfide, 3,3'-dibromo-4,4'-diaminodiphenylsulfide, 3,3'-dicarboxyl-4,4'-diaminodiphenylsulfide, 3,3'-dihydroxy-4,4'-diaminodiphenylsulfide, 3,3'-disulfo-4,4'-diaminodiphenylsulfide, 3,3'-dimethyl-4,4'-diaminodiphenylsulfone, 3,3'-diethoxy-4,4'-diaminodiphenylsulfone, 3,3'-dichloro-4,4'-diaminodiphenylfulfone, 3,3'-dicarboxy-4,4'-diaminodiphenylsulfone, 3,3'-dihydroxy-4,4'-diaminodiphenylsulfone, 3,3'-disulfo-4,4'-diaminodiphenylsulfone, 3,3'-diethyl-4,4'-diaminodiphenylpropane, 3,3'-dimethoxy-4,4'-diaminodiphenylpropane, 3,3'-dichloro-4,4'-diaminodiphenylpropane, 3,3'-dicarboxy-4,4'-diaminodiphenylpropane, 3,3'-dihydroxy-4,4'-diaminodiphenylpropane, 3,3'-disulfo-4,4'-diaminodiphenylpropane, 3,3'-dimethyl-4,4'-diaminobenzophenone, 3,3'-dimethoxy-4,4'-diaminobenzophenone, 3,3'-dichloro-4,4'-diaminobenzophenone, 3,3'-dibromo-4,4'-diaminobenzophenone, 3,3'-dicarboxy-4,4'-diaminobenzophenone, 3,3'-dihydroxy-4,4'-diaminobenzophenone, 3,3'-disulphodiaminobenzophenone, 3,3'-diaminodiphenylmethane, 3,3'-diaminodiphenylether, 3,3'-diaminodiphenylsulfide, 3,3'-diaminodiphenylsulfone, 3,3'-diaminodiphenylpropane, 3,3'-diaminobenzophenone, 2,4-diaminotoluene, 2,6-diaminotoluene, 1-isopropyl-2,4-phenylenediamine, diaminoanisole, 2,4-diaminomonochlorobenzene, 4,4-diaminofluorobenzene, 2,4-diaminobenzoic acid, 2,4-diaminophenol and 2,4-diaminobenzenesulfonic acid and phenylene diamines. Preferred diamines are 4,4'-oxydianiline, 4,4'-sulfonyldianiline, 4,4'-methylene dianiline, 4,4'-diaminobenzophenone, 4,4; diaminostilbene and the phenylene diamines, 2,4-diaminotoluene and all the meta and para isomers of $H_2NC_6H_4OC_6H_4OC_6H_4NH_2$.

SPECIFIC EMBODIMENT

The practice of this invention is illustrated by the following examples. These examples are given merely by way of illustration and are not intended to limit the scope of the invention in any way nor the manner in which the invention can be practiced. Unless specifically indicated otherwise, parts and percentages are given as parts and percentages by weight.

EXAMPLE A

Synthesis of 4,4'-bis(4-chlorobenzenesulfonyl)diphenylether

In a one liter round-bottom flask equipped with a stirrer, nitrogen inlet tube and reflux condenser, the top of which is connected to a bubbler and caustic absorber, is placed 170.2 gm. (1 mole) of diphenyl ether, 422 gms. (2 moles) of 4-chlorobenzene sulfonyl chloride and 16 gms. (0.1 mole) anhydrous ferric chloride. The mixture is heated at 170°–175° C. for a period of six hours during which time the solution thickens noticeably. The material is then allowed to cool to room temperature and recrystallized from approximately twice its volume of acetone. The yield is 466 gms. (90%) of a product with a melting point (determined by DSC) of 164° C. The elemental analyses of C: 55.29%, S: 12.27% and Cl: 13.58% are in good agreement with the theoretical values C: 55.38%; H: 3.03%; O: 15.38%; Cl: 13.65% and S: 12.31% (MW 520) for a compound of the formula $(C_{24}H_{16}O_5Cl_2S_2)$, that is:

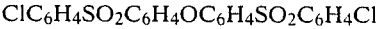
$ClC_6H_4SO_2C_6H_4OC_6H_4SO_2C_6H_4Cl$

The foregoing procedure is repeated a number of times using in place of the 4-chlorobenzene sulfonyl chloride equivalent amounts respectively of 4-chloro-3-methylbenzene sulfonyl chloride; 4-bromobenzene sulfonyl chloride; 4-chloro-naphthalene-1-sulfonyl chloride and 4′-chlorodiphenyl oxide-4-sulfonyl chloride. The following compounds are obtained respectively:

Cl—$C_6H_3(CH_3)SO_2C_6H_4OC_6H_4SO_2C_6H_3(CH_3)$—Cl
Br—$C_6H_4SO_2C_6H_4OC_6H_4SO_2C_6H_4$—Br
Cl—$C_{10}H_6SO_2C_6H_4OC_6H_4SO_2C_{10}H_6$—Cl
Cl—$C_6H_4OC_6H_4SO_2C_6H_4OC_6H_4SO_2C_6H_4OC_6H_4$—Cl

When the foregoing procedure is again repeated a number of times using in place of the diphenyl oxide equivalent amounts respectively of 3,3′-dimethyldiphenyl oxide, 1,1′-dinaphthylether and 4,4′-bis(phenoxy)diphenylether, the following compounds are obtained respectively:

Cl—$C_6H_4SO_2C_6H_3(CH_3)OC_6H_3(CH_3)SO_2C_6H_4$—Cl
Cl—$C_6H_4SO_2C_{10}H_6OC_{10}H_6SO_2C_6H_4$—Cl
Cl—$C_6H_4SO_2C_6H_4OC_6H_4OC_6H_4OC_6H_4SO_2C_6H_4$—Cl

EXAMPLE B

Synthesis of 4,4′-bis(4-chlorobenzenesulfonyl)diphenyl sulfone

Substitution of 218.2 gms. (1 mole) of diphenyl sulfone, $C_6H_5SO_2C_6H_5$ for the diphenyl oxide of Example I yields the corresponding compound $ClC_6H_4SO_2C_6H_4SO_2C_6H_4Cl$, having elemental analyses of 60.62% C and 16.69% S, which are in good agreement with the compound:
$C_{24}H_{16}O_6Cl_2S_3$ (MW 568)

The foregoing procedure is repeated a number of times using in place of the 4-chlorobenzene sulfonyl chloride equivalent amounts respectively of 4-chloro-3-methylbenzene sulfonyl chloride; 4-bromobenzene sulfonyl chloride; 4-chloro-naphthalene-1-sulfonyl chloride and 4-chloro-diphenyloxide-4′-sulfonyl chloride. The following compounds are obtained respectively:

Cl—$C_6H_3(CH_3)SO_2C_6H_4SO_2C_6H_4SO_2C_6H_3(CH_3)$—Cl
Br—$C_6H_4SO_2C_6H_4SO_2C_6H_4SO_2C_6H_4$—Br
Cl—$C_{10}H_6SO_2C_6H_4SO_2C_6H_4SO_2C_{10}H_6$—Cl
Cl—$C_6H_4OC_6H_4SO_2C_6H_4SO_2C_6H_4SO_2C_6H_4OC_6$-$H_4$—Cl

When the foregoing procedure is again repeated a number of times using in place of the diphenyl sulfone equivalent amounts respectively of 3,3′-dimethyldiphenylsulfone; 1,1′-dinaphthylsulfone and 4,4′-bis(phenoxy)diphenylsulfone. The following compounds are obtained respectively:

Cl—$C_6H_4SO_2C_6H_3(CH_3)SO_2C_6H_3(CH_3)SO_2C_6H_4$—Cl
Cl—$C_6H_4SO_2C_{10}H_6SO_2C_{10}H_6SO_2C_6H_4$—Cl
Cl—$C_6H_4SO_2C_6H_4OC_6H_4SO_2C_6H_4OC_6H_4SO_2C_6$-$H_4$—Cl

EXAMPLE Ia

Synthesis of Diesters of the Formula ROOCArO-A-OArCOOR

Into a one liter flask equipped with a stirrer, a Dean-Stark trap and a nitrogen gas inlet tube is placed 214 gms. (1 mole) of para-hydroxy phenyl benzoate, $HOC_6H_4COOC_6H_5$ and 40 gms. (1 mole) of sodium hydroxide dissolved in 500 ml. of 95% ethyl alcohol. The mixture is heated gently to distill off the ethyl alcohol until a solid phase begins to appear. Then 250 ml. of toluene and 250 ml. of dimethyl sulfoxide is added and the mixture is heated to reflux under nitrogen until no more water is collected in the Dean-Stark trap. The toluene is then distilled from the mixture and an additional 150 ml. of dimethyl sulfoxide is added. To this solution is added 260 gms. (0.5 mole) of 4,4′-bis(4-chlorobenzenesulfonyl)diphenylether and the mixture is heated with stirring under nitrogen for four hours at 160°–165° C. Then most of the dimethyl sulfoxide is recovered by distillation at 15 mm. Hg pressure in a rotary evaporator after which the residue is washed with hot water to extract sodium chloride. The crude product is dried in a vacuum oven at 15 mm. pressure for 24 hours and shows a melting point of 170°–173° C. A white sample recrystallized from alcohol-acetone solution shows elemental analyses of C: 67.73%; H: 3.74% and S: 7.48% which are in good agreement with a compound having the formula $C_{50}H_{34}O_{11}S_2$ and a molecular weight of 875, more specifically:

$H_5C_6OOCC_6H_4OC_6H_4SO_2C_6H_4OC_6H_4SO_2C_6$-$H_4OC_6H_4COOC_6H_5$.   (Ia)

EXAMPLE Ib

Substitution of 152.15 g. of para-hydroxy methyl benzoate, $HOC_6H_4COOCH_3$ (mole) for the equivalent amount of the phenyl ester of Example Ia yields the corresponding ester (MW 751) ($C_{40}H_{30}O_{11}S_2$):

$H_3COOCC_6H_4OC_6H_4SO_2C_6H_4OC_6H_4SO_2C_6$-$H_4OC_6H_4COOC_3$   (Ib)

EXAMPLE Ic

Substitution of 284 g. (0.5 mole) of 4,4′-bis(5-chlorobenzenesulfonyl)diphenyl sulfone for the 4-4-bis(4-chlorosulfonyl)diphenyl ether of Example Ia yields the corresponding ester (MW 923):

$H_5C_6OOCC_6H_4OC_6H_4SO_2C_6H_4SO_2C_6H_4SO_2C_6$-$H_4OC_6H_4COOC_6H_5$   (Ic)

EXAMPLE Id

Substitution of 248 g. (0.5 mole) of 4,4′-bis(4-chlorobenzene sulfonyl)diphenylsulfone for the 4,4-bis(4-chlorosulfonyl)ether of Example Ib yields the corresponding ester (MW 799):

$H_3COOCC_6H_4OC_6H_4SO_2C_6H_4SO_2C_6H_4SO_2C_6$-$H_4OC_6H_4COOCH_3$   (Id)

Various other esters of Formula I are similarly prepared by using hydroxy aryl esters of the formula HOArCOOR where R and Ar represent other hydrocarbon and aromatic groups, and also by using other X—A—X compounds having different Ar and Ar′ groups as described herein. For example, by using the appropriate hydroxy and ester compounds, the following compounds are easily prepared:

$CH_2=CHCH_2OOCC_6H_4OC_6H_4SO_2C_6H_4SO_2C_6H$-$_4SO_2C_6H_4OC_6H_4$—$COOCH_2CH=CH_2$   (Ie)

$CH_2=CHC_6H_4OOCC_6H_4OC_6H_4SO_2C_6H_4OC_6H_4$-$SO_2C_6H_4OC_6H_4COOC_6H_4CH=CH_2$   (If)

$HC\equiv CC_6H_4OOCC_6H_4OC_6H_4SO_2C_6H_4OC_6H$-$_4SO_2C_6H_4OC_6H_4COOC_6H_4C_6H_4C\equiv CH$   (Ig)

Hydrolysis of the products of Examples 1a through 1d, for example with aqueous NaOH solution, produces the respective diacids of the formula HOOCArO—A—OAr—COOH, for example:

$HOOCC_6H_4OC_6H_4SO_2C_6H_4OC_6H_4SO_2C_6$-$H_4OC_6H_4COOH$   (Ih)

and $$HOOCC_6H_4OC_6H_4SO_2C_6H_4SO_2C_6H_4SO_2C_6H_4OC_6H_4COOH \quad (Ii)$$

Where other Ar and Ar' groups are present the diacid compounds will differ accordingly.

The free diacids may be easily converted by reaction with thionyl halides, such as thionyl chloride (SOCl$_2$) or with phosphorus halides (PCl$_5$ or PCl$_3$) to give the corresponding diacid halides of the formula XOCAr—O—A—OArCOX. For example, reaction of compounds Ih and Ii with SOCl$_2$, under the usual conditions for such reactions, produces:

$$ClOCC_6H_4OC_6H_4SO_2C_6H_4OC_6H_4SO_2C_6H_4OC_6H_4COCl \quad (Ij)$$

and $$ClOCC_6H_4OC_6H_4SO_2C_6H_4SO_2C_6H_4SO_2C_6H_4OC_6H_4COCl \quad (Ik)$$

EXAMPLE II

Preparation of Diamides of Compound I having the Formula R$_2$NOCAr—O—A—OArCONR$_2$ To a one-liter flask equipped with a stirrer, a reflux condenser and a nitrogen atmosphere, with an ice water bath to control temperature, there is added 200 ml. of ether, 9.92 gms. (0.22 moles) of dimethyl amine and 17.7 gms. (0.3 moles) of trimethyl amine. The temperature is maintained at approximately 0° C. while a solution is slowly added which contains 63.5 gms. (0.1 mole) of the acid chloride Ij in ether. Stirring is continued for 30 minutes after the addition is completed. The resultant solution is decanted from the precipitated trimethylamine hydrochloride and the precipitate washed with ether with the ether wash being added to the product solution. The ether and excess trimethylamine and dimethylamine are evaporated from the product. Elemental analyses of 64.88% C and 4.61% H check closely with the theoretical values for the compound:

$$(CH_3)_2NOCC_6H_4OC_6H_4SO_2C_6H_4OC_6H_4SO_2C_6H_4OC_6H_4CON(CH_3)_2 \quad (IIa)$$

When the above procedure is repeated using an equivalent amount of the acid chloride Ik in place of the acid chloride Ij, there is obtained:

$$(CH_3)_2NOCC_6H_4OC_6H_4SO_2C_6H_4OC_6H_4SO_2C_6H_4OC_6H_4CON(CH_3)_2 \quad (IIb)$$

Repetition of the above procedure with various other amines of the formula R$_2$NH and appropriate modifications of conditions are used to prepare:

$$NH_2OCC_6H_4OC_6H_4SO_2C_6H_4OC_6H_4SO_2C_6H_4OC_6H_4CONH_2 \quad (IIc)$$

$$NH_2OCC_6H_4OC_6H_4SO_2C_6H_4SO_2C_6H_4SO_2C_6H_4OC_6H_4CONH_2 \quad (IId)$$

$$C_6H_5NHOCC_6H_4OC_6H_4SO_2C_6H_4OC_6H_4SO_2C_6H_4OC_6H_4CONHC_6H_5 \quad (IIe)$$

$$C_6H_{11}NHOCC_6H_4OC_6H_4SO_2C_6H_4SO_2C_6H_4SO_2C_6H_4OC_6H_4CONHC_6H_{11} \quad (IIf)$$

$$(C_2H_5)_2NOCC_6H_4OC_6H_4SO_2C_6H_4OC_6H_4SO_2C_6H_4OC_6H_4CON(C_2H_5)_2 \quad (IIg)$$

These amide derivatives may also be made from the acids Ih and Ii and also from the esters Ia–Id.

EXAMPLE III

Preparation of Polymeric Polyamides Having the Repeating Unit Formula $$-N(R)-R'-N(R)(O)CArO-A-OArC(O)- \quad (III)$$

Into a one-liter flask equipped with a stirrer, a Dean-Stark trap and a nitrogen gas inlet is placed 173.25 gms (0.25 mole) of the free acid Ih, 27 gms (0.25 mole) of phenylene diamine, 200 ml. of dimethyl sulfoxide and 200 ml. of toluene. The mixture is refluxed under nitrogen until no more water is collected in the Dean-Stark trap. Then the toluene is distilled from the mixture and films laid from the resulting polymer solution. Evaporation of the solvent leaves films of good hardness and heat resistance and elemental analyses show values of 66.46% C and 3.78% H which is in good agreement with repeating units of the formula:

$$-NHC_6H_4NHOCC_6H_4OC_6H_4SO_2C_6H_4OC_6H_4SO_2C_6H_4OC_6H_4CO- \quad (IIIa)$$

When the above procedure is repeated using acid Ii in place of Ih, the polymer repeating units have the formula:

$$-NHC_6H_4NHOCC_6H_4OC_6H_4SO_2C_6H_4SO_2C_6H_4SO_2C_6H_4OC_6H_4CO- \quad (IIIb)$$

When ethylene diamine is used in equivalent amounts in place of the phenylene diamine, the respective polymer units have the formulas $$-NHCH_2CH_2NHOCC_6H_4OC_6H_4SO_2C_6H_4OC_6H_4SO_2C_6H_4OC_6H_4CO- \quad (IIIc)$$

and $$-NHCH_2CH_2NHOCC_6H_4OC_6H_4SO_2C_6H_4SO_2C_6H_4SO_2C_6H_4OC_6H_4CO- \quad (IIId)$$

With diphenyldiamine, naphthalene diamine, 1,4 butylenediamine, cyclohexane-1,4-diamine, the respective polymer repeating units are:

$$-NHC_6H_4C_6H_4NHOCC_6H_4OC_6H_4SO_2C_6H_4OC_6H_4SO_2C_6H_4OC_6H_4CO-$$

$$-NHC_6H_4C_6H_4NHOCC_6H_4OC_6H_4SO_2C_6H_4SO_2C_6H_4SO_2C_6H_4OC_6H_4CO-$$

$$-NHC_{10}H_6NHOCC_6H_4OC_6H_4SO_2C_6H_4OC_6H_4SO_2C_6H_4OC_6H_4CO-$$

$$-NHC_{10}H_6NHOCC_6H_4OC_6H_4SO_2C_6H_4SO_2C_6H_4SO_2C_6H_4OC_6H_4CO-$$

$$-NH(CH_2)_3NHOCC_6H_4OC_6H_4SO_2C_6H_4OC_6H_4SO_2C_6H_4OC_6H_4CO-$$

$$-NH(CH_2)_3NHCC_6H_4OC_6H_4SO_2C_6H_4SO_2C_6H_4SO_2C_6H_4OC_6H_4CO-$$

$$-NHC_6H_{10}NHOCC_6H_4OC_6H_4SO_2C_6H_4OC_6H_4SO_2C_6H_4OC_6H_4CO-$$

$$-NHC_6H_{10}NHOCC_6H_4OC_6H_4SO_2C_6H_4SO_2C_6H_4SO_2C_6H_4OC_6H_4CO-$$

Replacement of the acids Ih and Ii in the foregoing procedures of Example III with other acids of Formula I produce other polymeric polyamides of this invention.

Examples of aromatic diamines which are suitable for the preparation of polyamides according to the procedure of Example III include 4,4'-diaminodiphenyl propane, 4,4'-diamino-diphenyl methane, benzidine, 3,3'-dichlorobenzidene, 4,4'-diamino-diphenyl sulfide, 3,3'-diamino-diphenyl sulfone, 4,4'-diamino-diphenyl sulfone, 4,4'-diamino-diphenyl ether, 1,4-diamino naphthalene, 4,4'-diamino-diphenyl diethylsilane, 4,4'-diamino-diphenyl diphenylsilane, 4,4'-diamino-diphenyl ethyl phosphine oxide, 4,4'-diamino-diphenyl phenyl phosphine 1,4-diamino naphthalene, 4,4'-diamino-diphenyl diethylsilane, 4,4'-diamino-diphenyl diphenylsilane, 4,4'-diamino-diphenyl ethyl phosphine oxide, 4,4'-diamino-diphenyl phenyl phosphine oxide, 4,4'-diamino-diphenyl N-methyl amine, 4,4'-diaminodiphenyl N-phenyl amine and mixtures thereof, 3,3'-dimethyl-4,4'-diaminodiphenylmethane, 3,3'-diethyl-4,4'-diaminodiphenylmethane, 3,3'-dimethoxy-4,4'-diaminodiphenylmethane, 3,3'-diethoxy-4,4'-diaminodiphenylmethane, 3,3'-dichloro-4,4',4,4'-diaminodiphenylmethane, 3,3'-dibromo-4,4'-diaminodiphenylmethane, 3,3'-dicarboxy-4,4'-diaminophenylmethane, 3,3'-dihydroxy-4,4'-diaminophenylmethane, 3,3'-disulpho-4,4'-diaminodiphenylmethane, 3,3'-dimethyl-4,4'diaminodiphenylether, 3,3'-diethyl-4,4'-diaminodiphenylether, 3,3'-dimethoxy-4,4'-diaminodiphenylether, 3,3'-disulfo-4,4'-diaminodiphenylether, 3,3'-dimethyl-4,4'-diaminodiphenylsulfide, 3,3'-diethyl-4,4'-diaminodiphenylsulfide, 3,3'-diemthoxy-4,4'-diaminodiphenylsulfide, 3,3'-diethoxy-4,4'-diaminodiphenylsulfide, 3,3'-dichloro-4,4'-diaminodiphenylsulfide, 3,3'-dibromo-4,4'-diaminodiphenylsulfide, 3,3'-dicarboxyl-4,4'-diaminodiphenylsulfide, 3,3'-dihydroxy-4,4'-diaminodiphenylsulfide, 3,3'-disulfo-4,4'-diaminodiphenylsulfide, 3,3'-dimethyl-4,4'-diaminodiphenylsulfone, 3,3'-diethoxy-4,4'-diaminodiphenylsulfone, 3,3'-dichloro-4,4'-diaminodiphenylsulfone, 3,3'-dicarboxy-4,4'-diaminodiphenylsulfone, 3,3'-dihydroxy-4,4'-diaminodiphenylsulfone, 3,3'-disulfo-4,4'-diaminodiphenylsulfone, 3,3'-diethyl-4,4'-diaminodiphenylpropane, 3,3'-dimethoxy-4,4'-diaminodiphenylpropane, 3,3'-dichloro-4,4'-diaminodiphenylpropane, 3,3'-dicarobxy-4,4'-diaminodiphenylpropane, 3,3'-dihydroxy-4,4'-diaminodiphenylpropane, 3,3'-disulfo-4,4'-diaminodiphenylpropane, 3,3'-dimethyl-4,4'-diaminobenzophenone, 3,3'-dimethoxy-4,4'-diaminobenzophenone, 3,3'-dichloro-4,4'-diaminobenzophenone, 3,3'-dibromo-4,4'-diaminobenzophenone, 3,3'-dicarboxy-4,4'-diaminobenzophenone, 3,3'-dihydroxy-4,4'-diaminobenzophenone, 3,3'-disulphodiaminobenzophenone, 3,3'-diaminodiphenylmethane, 3,3'-diaminodiphenylether, 3,3'-diaminodiphenylsulfide, 3,3'-diaminodiphenylsulfone, 3,3'-diaminodiphenylpropane, 3,3'-diaminobenzophenone, 2,4-diaminotoluene, 2,6-diaminotoluene, 1-isopropyl-2,4-phenylenediamine, 2,4-diaminoanisole, 2,4-diaminomonochlorobenzene, 2,4-diaminofluorobenzene, 2,4-diaminobenzoic acid, 2,4-diaminophenol and 2,4-diaminobenzenesulfonic acid, and phenylene diamines. Preferred diamines are 4,4'-oxydianiline, 4,4'-sulfonyldianiline, 4,4'-methylene dianiline, 4,4'-diaminobenzophenone, 4,4'-diaminostilbene and the phenylene diamines, 2,4-diaminotoluene and all the meta and para isomers of $H_2NC_6H_4OC_6H_4OC_6H_4NH_2$.

Aliphatic and cycloaliphatic diamines which are also suitable include: ethylene diamine, propylene diamine, 1,4-butylene diamine, 1,3-propylene diamine, 2,3-butylene diamine, 1,4-amylene diamine, 2,3-amylene diamine, pentamethylene diamine, hexamethylene diamine, $NH_2(CH_2CHRNH)_xH$, wherein X may have a value of 2-20 and R is as defined above, preferably hydrogen, cyclohexane-1,4-diamine, cycloheptane-1,4-diamine, cyclohexane-1,2-diamine, 1,4-bis(aminomethyl)cyclohexane, 1,2-bis(aminomethyl)cyclohexane, etc.

EXAMPLE IV

Polyesters Having the Repeating Unit Formula $$—OR'O(O)CArO—A—OArC(O)—$$  (IV)

The procedure of Example III is repeated using Ih and an equivalent amount of ethylene glycol in place of the phenyl diamine. A polyester polymer is obtained having a repeating unit structure having the formula:

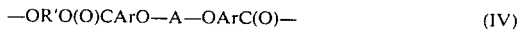
$—OCH_2CH_2OOCC_6H_4OC_6H_4SO_2C_6H_4OC_6H_4SO_2C_6H_4OC_6H_4C(O)—$ (IVa)

When the procedure is repeated using equivalent amounts respectively of propylene glycol, tetramethylene glycol, $HO(CH_2CH_2O)_4H$, hydroquinone, cyclohexane-1,4-diol and cyclohexane-1,4-dimethanol, polyesters are obtained having the following repeating unit structures respectively:

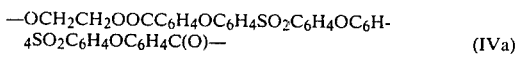
$—OCH_2CH(CH_3)OOCC_6H_4SO_2C_6H_4OC_6H_4C(O)—$ (IVb)

$—O(CH_2)_3OOCC_6H_4OC_6H_4SO_2C_6H_4OC_6H_4C(O)—$ (IVc)

$—O(CH_2CH_2O)_4OCC_6H_4OC_5H_4SO_2C_4H_3OC_6H_4SO_2C_5H_4OC_6H_4C(O)—$ (IVd)

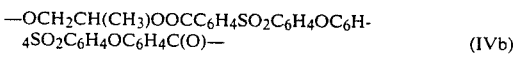
$—OC_6H_4OOCC_6H_4OC_6H_4SO_2C_6H_4OC_6H_4SO_2C_6H_4OC_6H_4C(O)—$ (IVe)

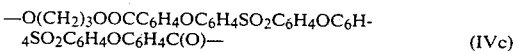
$—OC_6H_{10}OOCC_6H_4OC_6H_4SO_2C_6H_4OC_6H_4C(O)—$ (IVf)

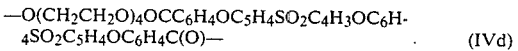
$—OCH_2C_6H_{10}CH_2OOCC_6H_4OC_6H_4SO_2C_6H_4OC_6H_4OC_6H_4C(O)—$ (IVg)

When the above procedures of Example IV are repeated using Ii in place of Ih, the following repeating unit structures are obtained respectively:

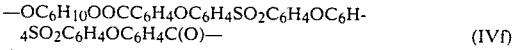
$—OCH_2CH(CH_3)OOCC_6H_4OC_6H_4SO_2C_6H_4SO_2C_6H_4OC_6H_4C(O)—$ (IVh)

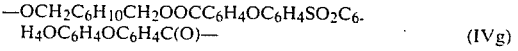
$—O(CH_2)_4OOCC_6H_4OC_6H_6SO_2C_6H_4SO_2C_6H_4OC_6H_4C(O)—$ (IVi)

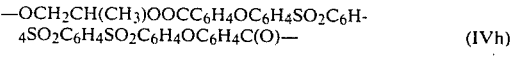
$—O(CH_2CH_2O)_4OCC_6H_4OC_6H_4SO_2C_6H_4SO_2C_6H_4OC_6H_4C(O)—$ (IVj)

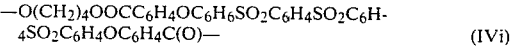
$—OC_6H_4OOCC_6H_4OC_6H_4SO_2C_6H_4SO_2C_6H_4OC_6H_4C(O)—$ (IVk)

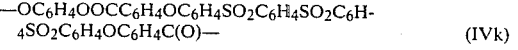
$—OC_6H_{10}OOCC_6H_4OC_6H_4SO_2C_6H_4SO_2C_6H_4OC_6H_4C(O)—$ (IVl)

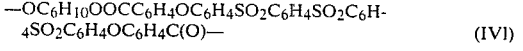
$—OCH_2C_6H_{10}CH_2OOCC_6H_4OC_6H_4SO_2C_6H_4SO_2C_6H_4OC_6H_4C(O)—$ (IVm)

Aliphatic, aromatic and cycloaliphatic glycols which are also suitable include: ethylene glycol, 1,2-propylene glycol, 1,4-butylene glycol, 1,3-propylene glycol, 2,3-butylene glycol, 1,4-amylene glycol, 2,3-amylene glycol, pentamethylene glycol, hexamethylene glycol, HO(CH₂CHRO)ₓH, wherein X may have a value of 2–20 and R is as defined above, preferably hydrogen, cyclohexane-1,4-diol, cycloheptane-1,4-diol, cyclohexane-1,2-diol, cyclohexane-1,4-dimethanol, cyclohexane-1,2-dimethanol, hydroquinone, resorcinol, p,p'-dihydroxydiphenyl, 1,4-dihydroxy-naphthalene, bis-phenol-A, dimethylolbenzene, dimethylolnaphthalene, dimethyloldiphenyl, etc.

In addition to replacing the glycols in the foregoing procedures of Example IV, the replacement of acids Ih and Ii with other acids of Formula I produce the corresponding polyester polymers of this invention.

EXAMPLE V

Preparation of Unsaturated Aromatic Ether Compounds Having the Formula

KO—A—OK (wherein K represents an aromatic group having a terminal vinyl or acetylene radical)    (V)

The procedure of Example I is repeated using 120 gms. (1 mole) of para-hydroxy styrene in place of the para-hydroxy phenyl benzoate. The product is recrystallized from alcohol-acetone solution and elemental analyses of 69.89% C and 4.35% H show close agreement with the values of:

CH₂=CHC₆H₄OC₆H₄SO₂C₆H₄OC₆H₄SO₂C₆H₄OC₆H₄CH=CH₂    (Va)

Repetition of this procedure using equivalent amounts respectively of p-allyl phenol, p-propargyl phenol, 4-vinyl-1-naphthol and 4'-vinyl-4-hydroxydiphenyl produce the following compounds:

CH₂=CHCH₂C₆H₄OC₆H₄SO₂C₆H₄OC₆H₄SO₂C₆H₄OC₆H₄CH₂CH=CH₂    (Vb)

CH≡CCH₂C₆H₄OC₆H₄SO₂C₆H₄OC₆H₄SO₂C₆H₄OC₆H₄CH₂C≡CH    (Vc)

CH₂=CHC₁₀H₆OC₆H₄SO₂C₆H₄OC₆H₄SO₂C₆H₄OC₁₀H₆CH=CH₂    (Vd)

CH₂=CHC₆H₄C₆H₄OC₆H₄SO₂C₆H₄OC₆H₄SO₂C₆H₄OC₆H₄C₆H₄CH=CH₂    (Ve)

Repetition of the above procedures using an equivalent amount of 4,4'-bis(4-chlorosulfonyl)diphenylsulfone in place of the corresponding diphenyl ether produces the following compounds:

CH₂=CHC₆H₄OC₆H₄SO₂C₆H₄SO₂C₆H₄SO₂C₆H₄OC₆H₄CH=CH₂    (Vf)

CH₂=CHCH₂C₆H₄OC₆H₄SO₂C₆H₄SO₂C₆H₄SO₂C₆H₄OC₆H₄CH₂CH=CH₂    (Vg)

CH≡CCH₂C₆H₄OC₆H₄SO₂C₆H₄SO₂C₆H₄SO₂C₆H₄OC₆H₄CH₂C≡CH    (Vh)

CH₂=CHC₁₀H₆OC₆H₄SO₂C₆H₄SO₂C₆H₄SO₂C₆H₄OC₁₀H₆CH=CH₂    (Vi)

CH₂=CHC₆H₄C₆H₄OC₆H₄SO₂C₆H₄SO₂C₆H₄SO₂C₆H₄OC₆H₄C₆H₄CH=CH₂    (Vj)

The compounds of Example V having two terminal vinyl (CH₂=CH—) or acetylene (CH≡C—) groups are polymerized to tough, infusible polymers using techniques known in the art for effecting addition polymerization, such as with free radical-generating catalysts. For example, 5 g of compound Va is dissolved in 20 gms. of dimethylacetamide and 0.05 gms. of benzoyl peroxide is added. The solution is maintained at 95°–105° C. for 3 hours. An insoluble, infusible polymer is obtained. Similar results are obtained when a portion of the Va compound is replaced with a vinyl or vinylidene comonomer as follows:

a. 80% Va plus 20% styrene
b. 90% Va plus 10% acrylonitrile
c. 90% Va plus 10% methyl methacrylate
d. 50% Va plus 50% styrene Similar results are also obtained when Va is replaced with corresponding amounts of compounds Vb through Vj respectively in each of the foregoing polymerizations.

EXAMPLE VI

Preparation of Aromatic Ether Compounds Having A Terminal Aromatic Hydroxy Group of the Formula HOArO—A—OArOH The procedure of Example Ia is repeated except that in place of the p-hydroxy phenyl benzoate there is used 110.11 gms. (1 mole) of hydroquinone, and the 4,4'-bis(4-chlorosulfonyl)diphenylether is added gradually over a period of one hour as a solution in the 150 mls of dimethyl sulfoxide which is to be added after removal of the toluene. The product is recrystallized from alcohol-acetone solution and the values from elemental analyses 64.51% C and 4.09% H are in good agreement for the compound:

HOC₆H₄OC₆H₄OC₆H₄SO₂C₆H₄OC₆H₄SO₂C₆H₄OC₆H₄OC₆H₄OH    (VIa)

By substituting equivalent amounts respectively of 1,4-dihydroxynaphthalene, 4,4'-dihydroxydiphenyl, bisphenol-A and diphenylol-methane the following compounds are prepared:

HOC₁₀H₆OC₆H₄SO₂C₆H₄OC₆H₄SO₂C₆H₅OC₁₀H₆OH    (VIb)

HOC₆H₄C₆H₄OC₆H₄SO₂C₆H₄OC₆H₄SO₂C₆H₄OC₆H₄C₆H₄OH    (VIc)

HOC₆H₄C(CH₃)₂C₆H₄OC₆H₄SO₂C₆H₄OC₆H₄SO₂C₆H₄OC₆H₄C(CH₃)₂C₆H₄OH    (VId)

HOC₆H₄CH₂C₆H₄OC₆H₄SO₂C₆H₄OC₆H₄SO₂C₆H₄OC₆H₄CH₂C₆H₄OH    (VIe)

When 4,4'-bis(4-chlorosulfonyl)diphenylsulfone is used in place of the corresponding diphenyl ether in the five above procedures, the following compounds are prepared:

HOC₆H₄OC₆H₄SO₂C₆H₄SO₂C₅H₄SO₂C₆H₄OC₆H₄OH    (VIf)

HOC₁₀H₆OC₆H₄SO₂C₆H₄SO₂C₆H₄SO₂C₆H₄OC₁₀H₆OH    (VIg)

HOC₆H₄C₆H₄OC₆H₄SO₂C₆H₄SO₂C₆H₄SO₂C₆H₄OC₆H₄C₆H₄OH    (VIh)

HOC₆H₄C(CH₃)₂C₆H₄OC₆H₄SO₂C₆H₄SO₂C₆H₄SO₂C₆H₄OC₆H₄C(CH₃)₂C₆H₄OH    (VIi)

HOC₆H₄CH₂C₆H₄OC₆H₄SO₂C₆H₄SO₂C₆H₄SO₂C₆H₄OC₆H₄CH₂C₆H₄OH    (VIj)

EXAMPLE VII

Aldehyde Condensation Polymers Having the Repeating Unit Formula

—CHR—Ar"(OH)O—A—OAr"(OH)—(wherein
Ar" is a trivalent aromatic radical)     (VII)

Into a one-liter flask equipped with a stirrer, condenser and a nitrogen gas inlet tube is placed 400 ml of dimethyl sulfoxide and 166.5 gms (0.25 mole) of [HOC$_6$H$_4$OC$_6$H$_4$SO$_2$C$_6$H$_4$]$_2$O (VIa) and 0.4 gm of triethylamine. In a separate flask there is placed 15 gms (equivalent to 0.5 mole CH$_2$O) of paraformaldehyde. A stream of nitrogen is fed into this flask and through a tube into the first flask below the surface of the solution therein. The solution in the first flask is stirred and maintained at 90° C. while a bunsen burner is applied to the second flask containing the paraformaldehyde. As the paraformaldehyde is sublimed it is carried by the stream of nitrogen into the solution in the first flask. After the transfer of the paraformaldehyde (or formaldehyde) has been completed, the temperature of the solution is maintained for another 4 hours. Most of the dimethyl sulfoxide is removed by distillation at 15 mm. Hg pressure in a rotary evaporator. The product is dried in a vacuum oven at 15 mm. pressure for 24 hours. Then the product is pulverized and placed in a compression mold and molded at 250° C. and 2500 psi to give a tough, insoluble, heat-resistant product.

Similar results are obtained with the dihydroxy compounds of VI b, c, d, e, f, g, h, i and j.

EXAMPLE VIII

Condensation Products Having the Formula

—OCArCOOArO—A—OArO—     (VIII)

The procedure of Example VII is repeated except that the addition of formaldehyde (paraformaldehyde) is omitted. Instead there is added gradually 48 gms. (0.25 mole) of terephthalyl dichloride and the triethylamine is replaced with powdered NaOH to react with the HCl given off by the reaction. The precipitated sodium chloride is removed by decantation or filtration. The recovered product gives a tough polymeric film in which the polymer has the repeating unit structure:

—OCC$_6$H$_4$COOC$_6$H$_4$O—C$_6$H$_4$SO$_2$C$_6$H$_4$OC$_6$H$_4$SO$_2$C$_6$H$_4$OC$_6$H$_4$O—     (VIIIa)

Elemental analyses give values of 66.25% C and 3.47% H which check closely with the theoretical values for the above formula.

The foregoing procedure is repeated a number of times using respectively the other aromatic hydroxy-terminated compounds of above Example VI, namely compounds VIb through VIj. Polymers are obtained having the following repeating unit structures respectively:

—OCC$_6$H$_4$COOC$_{10}$H$_6$O—
C$_6$H$_4$SO$_2$C$_6$H$_4$OC$_6$H$_4$SO$_2$C$_6$H$_4$OC$_{10}$H$_6$O—     (VIIIb)

—OCC$_6$H$_4$COOC$_6$H$_4$C$_6$H$_4$O—
C$_6$H$_4$SO$_2$C$_6$H$_4$OC$_6$H$_4$SO$_2$C$_6$H$_4$OC$_6$H$_4$C$_6$H$_4$O—     (VIIIc)

—OCC$_6$H$_4$COOC$_6$H$_4$C(CH$_3$)$_2$C$_6$H$_4$O—
C$_6$H$_4$SO$_2$C$_6$H$_4$OC$_6$H$_4$SO$_2$C$_6$H$_4$OC$_6$H$_4$C(CH$_3$)$_2$C$_6$H$_4$O—     (VIIId)

—OCC$_6$H$_4$COOC$_6$H$_4$CHC$_6$H$_4$O—
C$_6$H$_4$SO$_2$C$_6$H$_4$OC$_6$H$_4$SO$_2$C$_6$H$_4$OC$_6$H$_4$CH$_2$C$_6$H$_4$O—     (VIIIe)

—OCC$_6$H$_4$COOC$_6$H$_4$O—
C$_6$H$_4$SO$_2$C$_6$H$_4$SO$_2$C$_6$H$_4$SO$_2$C$_6$H$_4$OC$_6$H$_4$O—     (VIIIf)

—OCC$_6$H$_4$COOC$_{10}$H$_6$O—
C$_6$H$_4$SO$_2$C$_6$H$_4$SO$_2$C$_6$H$_4$SO$_2$C$_6$H$_4$OC$_{10}$H$_6$O—     (VIIIg)

—OCC$_6$H$_4$COOC$_6$H$_4$C$_6$H$_4$O—
C$_6$H$_4$SO$_2$C$_6$H$_4$SO$_2$C$_6$H$_4$SO$_2$C$_6$H$_4$OC$_6$H$_4$C$_6$H$_4$O—     (VIIIh)

—OCC$_6$H$_4$COOC$_6$H$_4$CH$_2$C$_6$H$_4$O—
.C$_6$H$_4$SO$_2$C$_6$H$_4$SO$_2$C$_6$H$_4$SO$_2$C$_6$H$_4$OC$_6$H$_4$CH$_2$C$_6$H$_4$O—     (VIIIi)

—OCC$_6$H$_4$COOC$_6$H$_4$C(CH$_3$)$_2$C$_6$H$_4$O—
C$_6$H$_4$SO$_2$C$_6$H$_4$SO$_2$C$_6$H$_4$SO$_2$C$_6$H$_4$OC$_6$H$_4$C(CH$_3$)$_2$C$_6$H$_4$O—     (VIIIj)

Similar polymers are also obtained when the terephthalyl dichloride is replaced with equivalent amounts respectively of 1,4-phthalyl dichloride; 2,3-naphthalene dicarboxydichloride, 1,4-naphthalene dicarboxydichloride, peri-naphthalene dicarboxydichloride, 3,4-diphenyl dicarboxydichloride, 4,4'-diphenyl dicarboxychloride, 4,4'-diphenyloxide dicarboxyldichloride, 4,4'-diphenyl methane dicarboxydichloride, 4,4'-diphenylsulfide dicarboxydichloride and 3,3'-diphenylsulfone dicarboxydichloride.

EXAMPLE IX

Condensation Products of Phenylol-Terminated Polysulfone Polymers with Phosgene to Give Polymers Having the Repeating Unit Formula —OCOArO—A—OArO—     (IX)

The procedure of Example VIII is repeated except that the terephthalyl dichloride is omitted and instead 25 gms. (0.25 mole) of phosgene is fed in gradually through a tube as the formaldehyde is fed in a nitrogen stream as described in Example VII. The resultant polymeric film has the repeating unit structure:

—OCOC$_6$H$_4$O—C$_6$H$_4$SO$_2$C$_6$H$_4$OC$_6$H$_4$SO$_2$C$_6$H$_4$OC$_6$H$_4$O—     (IXa)

Elemental analyses give values of 64.10% C and 3.39% H which correspond closely with the theoretical values for the preceding formula.

The foregoing procedure is repeated a number of times using respectively the other aromatic hydroxy-terminated compounds of above Example VI namely compounds VIb through VIj. Polymers are obtained having the following repeating unit structures respectively:

—OCOC$_{10}$H$_6$O—C$_6$H$_4$SO$_2$C$_6$H$_4$OC$_6$H$_4$SO$_2$C$_6$H$_4$OC$_{10}$H$_6$O—     (IXb)

—OCOC$_6$H$_4$C$_6$H$_4$O—C$_6$H$_4$SO$_2$C$_6$H$_3$OC$_6$H$_4$SO$_2$C$_6$H$_4$OC$_6$H$_4$O—     (IXc)

—OCOC$_6$H$_4$C(CH$_3$)$_2$C$_6$H$_4$—C$_6$H$_4$SO$_2$C$_6$H$_4$OC$_6$H$_4$SO$_2$C$_6$H$_4$OC$_6$H$_4$C(CH$_3$)$_2$C$_6$H$_4$O—     (IXd)

—OCOC$_6$H$_4$CH$_2$C$_6$H$_4$O—C$_6$H$_4$SO$_2$C$_6$H$_4$OC$_6$H$_4$SO$_2$C$_6$H$_4$OC$_6$H$_4$CH$_2$C$_6$H$_4$O—     (IXe)

—OCOC$_6$H$_4$O—C$_6$H$_4$SO$_2$C$_6$H$_4$SO$_2$C$_6$H$_4$SO$_2$C$_6$H$_4$OC$_6$H$_4$O—     (IXf)

—OCOC₁₀H₆O—C₆H₄SO₂C₆H₄SO₂C₆H₄SO₂C₆H₄OC₁₀H₆O— (IXg)

—OCOC₆H₄C₆H₄O—C₆H₄SO₂C₆H₄SO₂C₆H₄SO₂C₆H₄OC₆H₄C₆H₄O— (IXh)

—OCOC₆H₄C(CH₃)₂C₆H₄O—C₆H₄SO₂C₆H₄SO₂C₆H₄OC₆H₄C(CH₃)₂C₆H₄O— (IXi)

—OCOC₆H₄CH₂C₆H₄O—C₆H₄SO₂C₆H₄SO₂C₆H₄SO₂C₆H₄OC₆H₄CH₂C₆H₄O— (IXj)

Similar results in producing polycarbonate polymers are also obtained when the phosgene is replaced with equivalent amounts respectively of diaryl carbonates, namely diphenyl carbonate, ditolyl carbonate, dinaphthyl carbonate, di(diphenyl)carbonate, etc., preferably in the presence of zinc acetate dihydrate (0.25%) and at a temperature of 190°–195° C. The phenol or other by-product is removed by distillation.

EXAMPLE X

Reaction of Compounds I with Dihydroxy Compounds VI to Prepare Polyesters Having the Repeating Unit Formula —(O)CArO—A—OArC(O)OArO—A—OArO— (X)

Compounds I, namely [DOOCArOArSO₂Ar']₂Q, in either acid, ester or acid halide form may be reacted with compound VI, namely [HOArOArSO₂Ar']₂Q to replace the D group with polyester linkages between said compounds to prepare polymers having repeating units of the formula:

—OCArO—ArSO₂Ar'QAr'SO₂ArOAr-
COOArOArSO₂Ar'QAr'
SO₂ArOArO— (X)

Thus 150.0 gms. (0.2 mole) of

[CH₃OOCC₆H₄OC₆H₄SO₂C₆H₄]₂O (Ib)

and 142.8 (0.2 mole of

[HOC₆H₄OC₆H₄SO₂C₆H₄]₂SO₂ (VIf)

are added to a one liter flask equipped with stirrer, nitrogen inlet tube and Dean-Stark trap, containing 300 ml. of dimethyl sulfoxide and 7.5 gms. of zinc acetate dihydrate. This mixture is heated gradually up to 190° C. and maintained at 190°–195° C. for two hours during which time almost the theoretical amount of methanol is collected. The polymer product is recovered by removing most of the dimethyl sulfoxide by distillation at 15 mm Hg pressure in a rotary evaporator. A film obtained from the viscous concentration of the polymer is dried in a vacuum oven at 15 mm pressure for 24 hours. The polymer film is tough and heat-resistant. Elemental analyses give values of 63.33% C and 3.39% H which values check closely with the theoretical values for the polymer having a repeating unit structure of the formula:

—OCC₆H₄O—C₆H₄SO₂C₆H₄OC₆H₄SO₂C₆H₄OC₆H₄COOC₆H₄OC₆H₄SO₂C₆H₄SO₂C₆H₄SO₂C₆H₄OC₆H₄O— (Xa)

The above procedure is repeated a number of times using equivalent amounts respectively of the following combinations:
 (b) Ic and VIa
 (c) Id and VIc
 (d) Ie and VId
 (e) If and VIe
 (f) Ig and VIg
 (g) Ii and VIh Similar polymers fitting the above repeating unit X are obtained in each case. Similar polymers are obtained also when the I compounds are reacted in the acid and acid chloride forms with appropriate modifications made in the reaction conditions.

EXAMPLE XI

Preparation of Diamines Having the Formula

NR₂ArO—A—OArNR₂ (XI)

Into a 500 ml flask equipped with a stirrer, Dean-Stark trap, and nitrogen inlet tube is placed 66.1 gms. (0.606 moles) of para-aminophenol, and 24 gms. (0.6 mole) of sodium hydroxide dissolved in 25 ml of water. Approximately 100 ml of toluene and 100 ml of dimethylsulfoxide is then added. This mixture is heated to reflux under nitrogen and the water removed by the Dean-Stark trap. When no more water is collected in the trap, toluene is distilled from the mixture and an additional 100 ml of dimethylsulfoxide is added. To this solution is added 156.6 gms. (0.30 mole) of 4,4'-bis(4-chlorobenzenesulfonyl)diphenyl ether prepared according to Example A. This mixture is stirred under nitrogen while the temperature is maintained for one hour and 25 minutes at 160° C. and then cooled to room temperature. The resulting solution is diluted with 2.5 liters of water and made basic (pH approximately 8.0) with sodium hydroxide. Precipitation of the crude product is effected upon the addition of the sodium hydroxide. The precipitate is collected, washed with water and redissolved in 3 liters of dilute hydrochloric acid. This solution is slowly neutralized with sodium hydroxide to reprecipitate the product. After collecting the product on a Buchner funnel, it is washed again with cold water and dried in a vacuum to yield 131 gms. (65%) of a creamed colored product having a DSC melting point of 265° C. Elemental analyses of 65.4% C and 4.19% H check closely with the values for the formula:

H₂NC₆H₄OC₆H₄SO₂C₆H₄OC₆H₄SO₂C₆H₄OC₆H₄NH₂ (XIa)

Replacement of the 4,4'-bis(4-chlorobenzenesulfonyl)-diphenyl ether with equivalent amounts respectively of:
 (b) [Cl—C₆H₃(CH₃)SO₂C₆H₄]₂O
 (c) [Cl—C₁₀H₆SO₂C₆H₄]₂O
 (d) [Cl—C₆H₄OC₆H₄SO₂C₆H₄]₂O
 (e) [Cl—C₆H₄SO₂C₆H₄]₂SO₂
 (f) [Cl—C₁₀H₆SO₂C₆H₄]₂SO₂
 (g) [Cl—C₆H₄C₆H₄OC₆H₄SO₂C₆H₄]₂SO₂
produce the following compounds respectively:

[H₂NC₆H₄OC₆H₃(CH₃)SO₂C₆H₄]₂O (XIb)

[H₂NC₆H₄OC₆H₃(CH₃)SO₂C₆H₄]O (XIc)

[H₂NC₆H₄OC₆H₄OC₆H₄SO₂C₆H₄]₂O (XId)

[H₂NC₆H₄OC₆H₄SO₂C₆H₄]₂SO₂ (XIe)

[H₂NC₆H₄OC₁₀H₆SO₂C₆H₄]₂SO₂ (XIf)

[H₂NC₆H₄OC₆H₄C₆H₄OC₆H₄SO₂C₆H₄]₂SO₂ (XIg)

When in the procedure for XIa the p-aminophenol is replaced with an equivalent amount respectively of 1-aminonaphthol-4, 4-NH₂-4′-hydroxydiphenyl and 4-NH₂-4′-hydroxydiphenyl oxide, the following products are prepared respectively:

[H₂NC₁₀H₆OC₆H₄SO₂C₆H₄]₂O (XIh)

[H₂NC₆H₄C₆H₄OC₆H₄SO₂C₆H₄]₂O (XIi)

[H₂NC₆H₄OC₆H₄OC₆H₄SO₂C₆H₄]₂O (XIj)

EXAMPLE XII

Condensation of Dicarboxy Compound I with Diamine Compound XI to Produce Polyamides Having Repeating Units of the Formula —N(R)ArO—A—OArN(R)(O)CArO—A—OArC-(O)— (XII)

Into a one liter flask equipped with a stirrer, condenser and a nitrogen gas inlet tube is placed 200 ml. of dimethyl sulfoxide, 177.5 gms. (0.25 mole) of [NH₂C₆H₄OC₆H₄SO₂C₆H₄]₂SO₂ (XIe) and 30 gms. (0.3 mole) of triethyl amine. Under a nitrogen atmosphere and with stirring, a solution is gradually added comprising 200 ml. of dimethyl sulfoxide containing 201.75 gms. (0.25 mole) of [ClOCC₆H₄OC₆H₄SO₂C₆H₄]₂SO₂ (Ik). After completion of the addition, the temperature is raised to and maintained at 90° C. for 2 hours. Then the solution is extracted with two 200 ml. portions of hot water to remove triethylamine hydrochloride and free triethyl amine. The dimethyl sulfoxide product solution is then placed in a rotary evaporator and most of the dimethyl sulfoxide is removed by distillation at 15 mm. Hg pressure. The polymer product is dried in a vacuum oven at 15 mm. pressure for 24 hours. Elemental analyses show values of 60.46% C and 3.38% H which check closely with a polyamide repeating unit structure of the formula:

—NHC₆H₄OC₆H₄SO₂C₆H₄SO₂C₆H₄SO₂C₆-
H₄OC₆H₄
NHOCC₆H₄OC₆H₄SO₂C₆H₄SO₂C₆H₄SO₂C₆H-
₄SO₂C₆H₄OC₆H₄CO— (XIIa)

Films of this polymer material show toughness and heat resistance. Other polyamides may be made similarly from the above procedure using other combinations of XI and I compounds, for example:

Ij with XIa
Ij with XIb
Ij with XIc
Ij with XId
Ik with XIf
Ik with XIg
Ik with XIh
Ik with XIi
Ik with XIj Moreover similar polyamides are made using the XI diamines with the diacids such as Ih and Ii and with the diesters such as Ia through Ic with appropriate modifications in conditions.

EXAMPLE XIII

Preparation of Ketones of the Formula

R″COArO—A—OArCOR″ (XIII)

(wherein R″ is a hydrocarbon group of 1–20 carbon atoms)

The procedure of Example I is repeated using in place of the p-hydroxy phenyl benzoate, 1 mole (136 gms.) of p-hydroxy acetophenone. The product recrystallized from alcohol-acetone solution shows elemental analyses of 66.78% C and 4.18% H agreeing closely with the compound of the formula:

[CH₃COC₆H₄OC₆H₄SO₂C₆H₄]₂O (XIIIa)

Replacement of the p-hydroxy acetophenone with equivalent amounts respectively of p-hydroxy-3-methyl-acetophenone, 1-hydroxy-6-acetyl-naphthalene, 4-hydroxy-4′-acetyl-diphenyl and 4-hydroxy-5′-benzoyl-diphenyl oxide produce the following compounds respectively:

[CH₃COC₆H₃(CH₃)OC₆H₄SO₂C₆H₄]₂O (XIIIb)

[CH₃COC₁₀H₆OC₆H₄SO₂C₆H₄]₂O (XIIIc)

[CH₃COC₆H₄C₆H₄OC₆H₄SO₂C₆H₄]₂O (XIIId)

[C₆H₅COC₆H₄OC₆H₄OC₆H₄SO₂C₆H₄]₂O (XIIIe)

When the 4,4′-bis(4-chlorobenzenesulfonyl)diphenyl ether is replaced with an equivalent amount of 4,4′-bis(4-chlorobenzenesulfonyl)diphenyl sulfone in each of the preceding procedures of Example XIII, the following compounds are obtained:

[CH₃COC₆H₄OC₆H₄SO₂C₆H₄]₂SO₂ (XIIIf)

[CH₃COC₆H₃(CH₃)OC₆H₄SO₂C₆H₄]₂SO₂ (XIIIg)

[CH₃COC₁₀H₆OC₆H₄SO₂C₆H₄]₂SO₂ (XIIIh)

[CH₃COC₆H₄C₆H₄OC₆H₄SO₂C₆H₄]₂SO₂ (XIIIi)

[C₆H₅COC₆H₄OC₆H₄OC₆H₄SO₂C₆H₄]₂SO₂ (XIIIj)

The acetyl groups in the above Example XIII products may be converted to the acetylene-terminated compounds of Example V, namely Vc and Vh. These diacetyl compounds, such as XIIIa, b, c, d, f, g, h and i, are reacted with 2 moles of PCl₅ in 282 gms. (4 moles) of dimethylformamide (DMF) and 80 gms. (2 moles) of NaOH per mole of the diacetyl compound to give the acetylene-terminated compounds of this invention such as Vc and Vh, which are capable of being polymerized to tough, heat and solvent resistant polymers by means of free radical-generating catalysts.

EXAMPLE XIV

Preparation of Tetracarboxylic Derivatives (DOOC)₂ArO—A—OAr(COOD)₂ (XIV)

The procedure of Example Ia is repeated using 210.19 gm. (1 mole) of 4-hydroxy-dimethylphthalate. Elemental analyses of the recrystallized product gives values of 60.89% C and 3.91% H which correspond closely with the calculated values for the compound of the formula

[(CH3OOC)2C6H3O—C6H4SO2C6H4]2O  (XIVa)

Repetition of this procedure using (Cl—C6H4SO2C6H4)2SO2 as the X—A—X component yields a product whose elemental analyses of 57.69% C and 37.40% H check closely with the compound having the formula

[(CH3OOC)2C6H3O—C6H4SO2C6H4]2SO2  (XIVb)

Corresponding results are obtained using the diethyl, divinyl, dipropargyl, dicyclohexyl esters as starting materials in place of the 4-hydroxy-dimethylphthalate, and also when other X—A—X compounds are used in place of those used above.

Hydrolysis of XIVa and XIVb with aqueous NaOH solution produces the respective free acids:

[(HOOC)2C6H3O—C6H4SO2C6H4]2O  (XIVa)

and

[(HOOC)2C6H3O—C6H4SO2C6H4]2SO2  (XIVb)

Reaction of these free acids with thionyl chloride gives the corresponding acid chlorides:

[(ClOOC)2C6H3O—C6H4SO2C6H4]2O  (XIVc)

and

[(ClOOC)2C6H3O-C6H4SO2C6H4]2SO2  (XIVd)

When these XIV compounds are reacted with NHR2 amines under amidation conditions, the amides XIVe are prepared. With diamines, the amidation products are polymeric polyamides XIVf, whose formula is given above.

EXAMPLE XV

Preparation of Dianhydride of Formula

O(OC)2ArO—A—OAr(CO)2O  (XV)

One hundreth mole (8.1 gms.) of the tetracid XIVa dissolved in 25 ml of dimethyl sulfoxide is placed under a nitrogen atmosphere in a 100 ml three-neck round bottom flask equipped with a magnetic stirrer, thermometer, condenser, gas inlet tube and dropping funnel. Then 4.1 gms. (0.04 mole) of acetic anhydride is added and the mixture refluxed for one hour. Then the apparatus is arranged for distillation and distillation conducted for essentially complete removal of excess acetic anhydride and by-product acetic acid. The remaining solution contains the dianhydride having the formula:

O(OC)2C6H3OC6H4SO2C6H4OC6H4SO2C6H4OC6H3(CO)2O  (XVa)

Elemental analyses of 61.93% C and 2.80% H check closely with the theoretical values for this formula. This solution is cooled to room temperature and a solution of 1.08 gms. (0.01 mole) of p-phenylenediamine in 15 ml of dimethylsulfoxide is added gradually over a period of 15 minutes. The reaction, which is exothermic, is maintained at 40° C. during the addition, and then at 85°–90° C. for 15 minutes. The intermediate at this point has the amic acid repeating unit structure:

—NHC6H4NHOCC6H3OC6H4SO2C6H4OC6H4SO2C6H4OC6H3CO—  (XVb)
            |                                                          |
           HOOC                            COOH

To this solution is added 3.06 gm. (0.03 mole) of acetic anhydride and the mixture is heated at 125° C. for 1.5 hours. Then the solvents are removed in a rotary flash evaporator. The residual solid is washed with anhydrous ether and dried in a vacuum oven. Elemental analyses values of C:65.12% and H:3.02% are in good agreement with the calculated values for the polymeric repeating unit structure:

>NC6H4N(OC)2C6H3OC6H4SO2C6H4OC6H4SO2C6H4OC6H3(CO)2<  (XVc)

When the foregoing procedure is repeated using dianhydride compound XIVb in place of XIVa, the resultant polymer has the repeating unit formula:

>NC6H4N(OC)2C6H3OC6H4SO2C6H4SO2C6H4SO2C6H4OC6H3(CO)2<  (XVd)

for which the elemental analyses of 61.68% C and 2.85% H agree closely with the calculated values. Films of these polymers are tough and show good solvent and heat resistance.

When the foregoing procedures are repeated with other dianhydrides of this invention and with other diamines, similar polymeric polysulfone polyimides are obtained.

The various compositions and derivatives described above may be represented by the formula:

M—ArSO2Ar'QAr'SO2Ar—M wherein Ar, Ar' and Q are as defined above and M represents the various groups described above.

When M is monovalent the M—A—M compound is mononomeric, such as, for example, when M represents the following groups:

| | | |
|---|---|---|
| (a) | DOOCArO— | (from formula I) |
| (b) | R2NOCArO— | (from formula II) |
| (c) | KO— | (from formula V) wherein K is an aromatic group having terminal CH2=CH— or CH≡C— |
| (d) | HOArO— | (from formula VI) |
| (e) | NR2ArO— | (from formula XI) |
| (f) | R"C(O)ArO— | (from formula XIII) |
| (g) | (DOOC)2ArO— | (from formula XIV) |
| (h) | O(OC)2ArO— | (from formula XV) |

When M is divalent the M—A—M composition may be polymeric with repeating units of the following respective formulas:

(i)   —NR—R'—NR(O)CArO—A—OArC(O)—   (from formula III)

-continued

| | | |
|---|---|---|
| (j) | —OR'O(O)CArO—A—OArC(O)— | (from formula IV) |
| (k) | —CHRAr"(OH)O—A—OAr"(OH)— | (from formula VII) |
| (l) | —(O)CArC(O)OArO—A—OArO— | (from formula VIII) |
| (m) | —(O)COArO—A—OArO— | (from formula IX) |
| (n) | —(O)CArO—A—OArC(O)OArO—A—OArO— | (from formula X) |
| (o) | —N(R)ArO—A—OArN(R)(O)CArO—A—OArC(O)— | (from formula XII) |

Typical polymeric forms may be represented by the following respective formulas which also show terminally attached groups in accordance with the methods of preparation shown in the respective examples:

higher values of either, the compound is a polymer having a plurality of repeating units.

These represent five ways of writing formulas for the same compound whereby the arrangement of the re- (i') H—[NHC$_6$H$_4$NH(O)CC$_6$H$_4$OC$_6$H$_4$SO$_2$C$_6$H$_4$OC$_6$H$_4$SO$_2$C$_6$H$_4$OC$_6$H$_4$C(O)—]$_n$OH
(from Example III)
or in the generic form
H—[NR—R'—NR(O)CArO—A—OArC(O)—]$_n$OH (j') H—[OCH$_2$CH$_2$O(O)CC$_6$H$_4$OC$_6$H$_4$SO$_2$C$_6$H$_4$OC$_6$H$_4$SO$_2$C$_6$H$_4$OC$_6$H$_4$C(O)—]$_n$OH
(from Example IV)
or in the generic form
H—[OR'O(O)CArO—A—OCArC(O)—]$_n$OH (k') HO—[CH$_2$—C$_6$H$_3$(OH)OC$_6$H$_4$SO$_2$C$_6$H$_4$OC$_6$H$_4$SO$_2$C$_6$H$_4$OC$_6$H$_3$(OH)—]$_n$H
(from Example VII)
or in the generic form
HO[CH(R)Ar"(OH)O—A—OAr"(OH)—]$_n$H (l') Cl—[(O)CC$_6$H$_4$C(O)C$_6$H$_4$OC$_6$H$_4$SO$_2$C$_6$H$_4$OC$_6$H$_4$SO$_2$C$_6$H$_4$OC$_6$H$_4$O—]$_n$H
(from Example VIII)
or in the generic form
Cl—[(O)CArC(O)ArO—A—OArO—]$_n$H (m') Cl—[(O)COC$_6$H$_4$OC$_6$H$_4$SO$_2$C$_6$H$_4$OC$_6$H$_4$SO$_2$C$_6$H$_4$OC$_6$H$_4$O—]$_n$H
(from Example IX)
or in the generic form
Cl—[(O) COArO—A—OArO—]$_n$H (n') CH$_3$O—[(O)CC$_6$H$_4$OC$_6$H$_4$SO$_2$C$_6$H$_4$OC$_6$H$_4$SO$_2$C$_6$H$_4$OC$_6$H$_4$C(O)O—
—C$_6$H$_4$OC$_6$H$_4$SO$_2$C$_6$H$_4$SO$_2$C$_6$H$_4$SO$_2$C$_6$H$_4$OC$_6$H$_4$O—]$_n$H
(from Example X)
or in the generic form
D—[(O)CArO—A—OArC(O)OArO—A—OArO—]$_n$H (o') H[—NHC$_6$H$_4$OC$_6$H$_4$SO$_2$C$_6$H$_4$SO$_2$C$_6$H$_4$SO$_2$C$_6$H$_4$OC$_6$H$_4$NH—
(O)CC$_6$H$_4$OC$_6$H$_4$SO$_2$C$_6$H$_4$SO$_2$C$_6$H$_4$SO$_2$C$_6$H$_4$OC$_6$H$_4$C(O)]$_n$—Cl
(from Example XII)
or in the generic form
H[—N(R)ArO—A—OArN(R)(O)CArO—A—OArC(O)—]$_n$Cl In the above formulas, n is an integer having a value of 1-50 or more preferably 1-20. When n equals 1, the compound is monomeric and when n equals 2 or more, the composition is polymeric. In either case the terminal valencies may be satisfied with various groups such as may be on the starting compounds or derived therefrom such as H, R, RCO, etc. Again the terminal groups will depend on the manner in which the repeating unit structure is recited or divided. For example, in the generic formula j' which is given above as (1) H—[OR'O(O)CArO—A—OCArC(O)—]$_n$OH
wherein n is 1-50 or more);
this may be rewritten several times as follows with n' which has a value of 0-49 or more, preferably 0-19.

(2) HOR'O(O)CArO-A-OCArC(O)[—ORO(O)CArO—A—OCArC(O)—]$_{n'}$OH (3) HOR'O(O)CArO[—A—OCArC(O)—ORO(O)CArO—]$_{n'}$A—OCArC(O)—OH (4) HOR'O[(O)CArO—A—OCArC(O)—OR'O]$_{n'}$-(O)CArO—A—OCArC(O)—OH (5) HOR'O(O)CArO—A—[OCArC(O)—OR'O(O)CArO—A—]$_{n'}$OCArC(O)—H

It may be seen therefore that various portions of the respective formulas may be taken as the repeating unit.

When n of formula (1) has a value of 1, the compound is monomeric and when n' of formulas (2) through (5) has a value of zero, the compound is monomeric. With peating unit is given a modified sequence and the terminal groups are modified accordingly. In these formulas the repeating unit as given within the brackets for formulas (2) through (5) may be selected almost arbitrarily thereby causing a variation in the terminal groups at the left and right ends of the respective formulas. While the formula arrangement of (1) is preferred, the various arrangements of (2) through (5) are permissible.

Moreover while the terminal groups are generally in the starting components, it is also possible that during the processing a terminal group may be converted to another group. For example, when an acid chloride is a terminal group in a starting component, the active chlorine at one terminal of the long chain may come into contact with water during processing and be converted to OH. Such reactive groups also may subsequently be deliberately converted to other groups, such as esters, by reaction with an alcohol.

It is preferred in the preparation of the above polymers that approximately equimolar amounts of the components or reagents should be used. In such cases the terminal group at one end will be derived from one component and the group at the other end will be derived from the other component. When one component or reagent is used in excess, the resultant polymer generally has both terminal groups derived from the component used in excess. However the use of a component in considerable excess will cause a limit on the molecular weight of the product and generally the more the excess the shorter will be the length of the resulting polymer molecule.

As disclosed above, the compositions of this invention hava a variety of utilities. For example, compositions of formulas I, II, VI, XI, XIII and XIV are particularly useful for blending with polyethylene terephthalate (PET) and polybutyleneterephthalate (PBT) to upgrade and improve their properties and also to improve their crystallization rates. Compositions of formulas V and XV can be used as intermediates in the formation of polymeric products of good properties. The polymeric compositions of formulas III, IV, VII, VIII, IX, X and XII give tough films and coatings of good heat and solvent resistance and may be molded to give products of excellent strength and work-loading properties. The polymeric compositions may be cured by heat and pressure with and without various fillers, modifiers, etc., to give shaped products of excellent properties.

In Example X, the polymers (b) through (g) have the following respective repeating unit formulas:

(b) $-(O)CC_6H_4OC_6H_4SO_2C_6H_4SO_2C_6H_4SO_2C_6H_4OC_6H_4C(O)-$
$OC_6H_4OC_6H_4OC_6H_4OC_6H_4SO_2C_6H_4OC_6H_4SO_2C_6H_4OC_6H_4OC_6H_4O-$ (c) $-(O)CC_6H_4OC_6H_4SO_2C_6H_4SO_2C_6H_4SO_2C_6H_4OC_6H_4C(O)-$
$OC_6H_4C_6H_4OC_6H_4SO_2C_6H_4OC_6H_4SO_2C_6H_4OC_6H_4C_6H_4O-$ (d) $-(O)CC_6H_4OC_6H_4SO_2C_6H_4OC_6H_4SO_2C_6H_4OC_6H_4C(O)-$
$OC_6H_4C(CH_3)_2C_6H_4OC_6H_4SO_2C_6H_4OC_6H_4SO_2C_6H_4OC_6H_4C(CH_3)_2C_6H_4O-$ (e) $-(O)CC_6H_4OC_6H_4SO_2C_6H_4OC_6H_4SO_2C_6H_4OC_6H_4C(O)-$
$OC_6H_4CH_2C_6H_4OC_6H_4SO_2C_6H_4OC_6H_4SO_2C_6H_4OC_6H_4CH_2C_6H_4O-$ (f) $-(O)CC_6H_4OC_6H_4SO_2C_6H_4OC_6H_4SO_2C_6H_4OC_6H_4C(O)-$
$OC_{10}H_6OC_6H_4SO_2C_6H_4SO_2C_6H_4SO_2C_6H_4OC_{10}H_6O-$ (g) $-(O)CC_6H_4OC_6H_4SO_2C_6H_4OC_6H_4SO_2C_6H_4OC_6H_4C(O)-$
$OC_6H_4C_6H_4OC_6H_4SO_2C_6H_4SO_2C_6H_4SO_2C_6H_4SO_2C_6H_4OC_6H_4C_6H_4O-$

In Example XII various polyamides produced therein have the following respective repeating units:

Ij with XIa:
$-NC_6H_4OC_6H_4SO_2C_6H_4OC_6H_4SO_2C_6H_4OC_6H_4NH-$
$(O)CC_6H_4OC_6H_4SO_2C_6H_4OC_6H_4SO_2C_6H_4OC_6H_4C(O)-$ Ij with XIb:
$-NHC_6H_4OC_6H_3(CH_3)SO_2C_6H_4OC_6H_4SO_2C_6H_3(CH_3)OC_6H_4NH-$
$(O)CC_6H_4OC_6H_4SO_2C_6H_4OC_6H_4SO_2C_6H_4OC_6H_4C(O)-$ Ij with XIc:
$-NHC_6H_4OC_6H_3(CH_3)SO_2C_6H_4OC_6H_4SO_2C_6H_3(CH_3)OC_6H_4NH-$
$(O)CC_6H_4OC_6H_4SO_2C_6H_4OC_6H_4SO_2C_6H_4OC_6H_4C(O)-$ Ij with XId:
$-NHC_6H_4OC_6H_4SO_2C_6H_4OC_6H_4SO_2C_6H_4OC_6H_4NH-$
$(O)CC_6H_4OC_6H_4SO_2C_6H_4OC_6H_4SO_2C_6H_4OC_6H_4C(O)-$ Ik with XIf:
$-NHC_6H_4OC_{10}H_6SO_2C_6H_4SO_2C_6H_4SO_2C_{10}H_6OC_6H_4NH-$
$(O)CC_6H_4OC_6H_4SO_2C_6H_4SO_2C_6H_4SO_2C_6H_4OC_6H_4C(O)-$ Ik with XIg:
$-NHC_6H_4OC_6H_4C_6H_4OC_6H_4SO_2C_6H_4SO_2C_6H_4SO_2C_6H_4OC_6H_4C_6H_4OC_6H_4NH-$
$(O)CC_6H_4OC_6H_4SO_2C_6H_4SO_2C_6H_4SO_2C_6H_4OC_6H_4C(O)-$ Ik with XIh:
$-NHC_{10}H_6OC_6H_4SO_2C_6H_4OC_6H_4SO_2C_6H_4OC_{10}H_6NH-$
$(O)CC_6H_4OC_6H_4SO_2C_6H_4SO_2C_6H_4SO_2C_6H_4OC_6H_4C(O)-$ Ik with XIi:
$-NHC_6H_4C_6H_4OC_6H_4SO_2C_6H_4OC_6H_4SO_2C_6H_4OC_6H_4C_6H_4NH-$
$(O)CC_6H_4OC_6H_4SO_2C_6H_4SO_2C_6H_4SO_2C_6H_4OC_6H_4C(O)-$ Ik with XIj:
$-NHC_6H_4OC_6H_4OC_6H_4SO_2C_6H_4OC_6H_4SO_2C_6H_4OC_6H_4OC_6H_4NH-$
$(O)CC_6H_4OC_6H_4SO_2C_6H_4SO_2C_6H_4SO_2C_6H_4OC_6H_4C(O)-$ In Example XIV amides XIVe have the following respective formulas:

From XIVa and XIVc:
$(R_2NOC)_2C_6H_3OC_6H_4SO_2C_6H_4OC_6H_4SO_2C_6H_4OC_6H_3(CONR_2)_2$ From XIVb and XIVd:
$(R_2NOC)_2C_6H_3OC_6H_4SO_2C_6H_4SO_2C_6H_4SO_2C_6H_4OC_6H_3(CONR_2)_2$ In this same Example XIV polymeric polyamides XIVf have the following typical repeating units:

$$\begin{array}{c}-N(R)(O)C\diagup\!\!\!\!\!^{C_6H_3OC_6H_4SO_2C_6H_4OC_6H_4SO_2C_6H_4OC_6H_3-C(O)N(R)-}\\-N(R)(O)C\qquad\qquad\qquad\qquad\qquad\qquad\qquad\qquad C(O)N(R)-\end{array}$$

and $$\begin{array}{c}-N(R)(O)C\diagup\!\!\!\!\!^{C_6H_3OC_6H_4SO_2C_6H_4SO_2C_6H_4SO_2C_6H_4OC_6H_3-C(O)N(R)-}\\-N(R)(O)C\qquad\qquad\qquad\qquad\qquad\qquad\qquad\qquad C(O)N(R)-\end{array}$$

While certain features of this invention have been described in detail with respect to various embodiments thereof, it will of course be apparent that other modifications can be made within the spirit and scope of this invention, and it is not intended to limit the invention to the exact details insofar as they are defined in the following claims.

The invention claimed is:

1. A polysulfone composition having the formula M—ArSO$_2$Ar'QAr'SO$_2$Ar—M wherein:

Ar and Ar' represent divalent aromatic groups and 2-5 of said divalent aromatic groups linked by O, S, C(O), N(R''), SO$_2$ or an aliphatic hydrocarbon group:

Q is either O or SO₂, and

M is a group selected from the class consisting of:
- (a) DOOCArO—
- (b) R₂NOCArO—
- (c) KO—
- (d) HOArO—
- (e) R″C(O)ArO—
- (f) (DOOC)₂ArO—
- (g) O(OC)₂ArO—
- (h) —NR—R′—NR(O)CArO—A—OArC(O)—
- (i) —OR′O(O)CArO—A—OArC(O)—
- (j) —CHRAr″(OH)O—A—OAr″(OH)—
- (k) —(O)CArC(O)OArO—A—OArO—
- (l) —(O)COArO—A—OArO—
- (m) —(O)CArO—A—OArC(O)OArO—A—OArO—
- (n) —N(R)ArO—A—OArN(R)(O)CAr—A—ArC(O)— wherein

Ar is as defined above:

D represents hydrogen, halogen or a monovalent hydrocarbon group of one to 20 carbon atoms;

R is a hydrogen or a hydrocarbon group or 2–5 of hydrocarbon groups joined by —O—, —S—, —COO—, —OOC— or —SO₂—;

R′ is a divalent hydrocarbon group;

R″ is a hydrocarbon group of 1–20 carbon atoms;

K is an aromatic group having a terminal vinyl or acetylene radical;

Ar″ is a trivalent aromatic group; and

A represents the divalent radical —ArSO₂Ar′QAr′-SO₂Ar—.

2. The composition of claim 1, having the formula DOOCArO—ArSO₂Ar′QAr′SO₂ArCOOD, wherein D, Ar and Q are as defined in claim 1.

3. The composition of claim 2, having the formula ROOCArO-ArSO₂Ar′QAr′SO₂ArCOOR, wherein D, Ar, Q and R are as defined in claim 1.

4. The composition of claim 2, in which R is CH₃.

5. The composition of claim 2, in which R is C₆H₅.

6. The composition of claim 4 in which Q is O.

7. The composition of claim 5 in which Q is O.

8. The composition of claim 4 in which Q is SO₂.

9. The composition of claim 5 in which Q is SO₂.

10. The composition of claim 2, in which D is H.

11. The composition of claim 10, in which Q is O.

12. The composition of claim 10, in which Q is SO₂.

13. The composition of claim 2, in which D is Cl.

14. The composition of claim 13, in which Q is O.

15. The composition of claim 13, in which Q is SO₂.

16. The composition of claim 1 having the formula R₂N(O)CArO—ArSO₂Ar′QAr′SO₂Ar—OArC(O)NR₂ wherein R, Ar′ and Q are as defined in claim 1.

17. The composition of claim 1 which has the formula H₂N(O)CArO—ArSO₂Ar′QAr′SO₂Ar—OArC(O)NH₂ wherein Ar, Ar′ and Q are as defined in claim 1.

18. The composition of claim 1 which has the formula KO—ArSO₂Ar′QAr′SO₂Ar—OK wherein K, Ar, Ar′ and Q are as defined in claim 1.

19. The composition of claim 1 which has the formula HOArO—ArSO₂Ar′QAr′SO₂Ar—O—ArOH, wherein K, Ar, Ar′ and Q are as defined in claim 1.

20. The composition of claim 1 which has the formula NR₂ArO—ArSO₂Ar′SO₂Ar′SO₂Ar—OArNR₂, wherein R, Ar and Ar′ are as defined in claim 1.

21. The composition of claim 1 which has the formula R″C(O)ArO—ArSO₂Ar′QAr′SO₂Ar—OArC(O)R″, wherein R″, Ar, Ar′ and Q are as defined in claim 1.

22. The composition of claim 1 which has the formula (DOOC)₂ArO—ArSO₂Ar′QAr′SO₂Ar—OAr(COOD)₂ wherein D, Ar, Ar′ and Q are as defined in claim 1.

23. The composition of claim 1 which has the formula O(OC)₂ArO—ArSO₂Ar′QAr′SO₂Ar—OAr(CO)₂O wherein Ar, Ar′ and Q are as defined in claim 1.

24. The composition of claim 1 which has the formula [—N(R)-R′—N(R)(O)CArOArSO₂Ar′QAr′-SO₂ArOArC(O)—]ₙ wherein n is an integer having a value of 1–50, and R, R′, Ar, Ar′ and Q are as defined in claim 1.

25. The composition of claim 1 which has the formula [—OR′O(O)CArO—ArSO₂Ar′QAr′SO₂ArOArC(O)—]ₙ wherein n is an integer having a value of 1–50, and R′, Ar, Ar′ and Q are as defined in claim 1.

26. The composition of claim 1 which has the formula [—CH(R)Ar″(OH)O—ArSO₂Ar′QArSO₂Ar—OAr′-(OH)—]ₙ wherein n is an integer having a value of 1–50 and R, Ar, Ar′, Ar″ and Q are as defined in claim 1.

27. The composition of claim 1 which has the formula [—(O)CArC(O)OArO—ArSO₂Ar′QAr′-SO₂Ar—OArO—]ₙ wherein n is an integer having a value of 1–50 and Ar, Ar′ and Q are as defined in claim 1.

28. The composition of claim 1 which has the formula [—(O)COArO—ArSO₂Ar′QAr′SO₂Ar—OArO—]ₙ wherein n is an integer having a value of 1–50 and Ar, Ar′ and Q are as defined in claim 1.

29. The composition of claim 1 which has the formula [—(O)CArO—ArSO₂Ar′QAr′SO₂Ar—OArC(O)OArO—ArSO₂Ar′QAr′SO₂Ar—OArO—]ₙ wherein n is an integer having a value of 1–50 and Ar, Ar′ and Q are as defined in claim 1.

30. The composition of claim 1 which has the formula [—N(R)ArO—ArSO₂Ar′QAr′SO₂Ar—OArN(R)(O)CAr—]ₙ wherein n is an integer having a value of 1–50 and R, Ar, Ar′ and Q are as defined in claim 1.

* * * * *

UNITED STATES PATENT AND TRADEMARK OFFICE
CERTIFICATE OF CORRECTION

PATENT NO. : 4,517,354
DATED : May 14, 1985
INVENTOR(S) : Gaetano F. D'Alelio

It is certified that error appears in the above-identified patent and that said Letters Patent is hereby corrected as shown below:

Col. 3, line 5, at the right end of the formula add a bond to the  so it will appear as 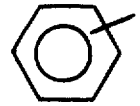 .

[Col. 3, line 65, change "additional" to read ---addition---.]

Col. 6, line 15, at the right end of the formula correct "$CO_{13}$" to read --- CO- ---.

Col. 27, line 5, correct "hava" to read ---have---.

Col. 29, line 21, change colon (:) to semicolon (;).

Col. 29, line 55, after "R," insert ---Ar,---.

Signed and Sealed this

Third Day of September 1985

[SEAL]

Attest:

DONALD J. QUIGG

Attesting Officer  Acting Commissioner of Patents and Trademarks - Designate